(12) United States Patent
Barrow et al.

(10) Patent No.: US 8,987,310 B2
(45) Date of Patent: Mar. 24, 2015

(54) HETEROCYCLE AMIDE T-TYPE CALCIUM CHANNEL ANTAGONISTS

(75) Inventors: James Barrow, Arnold, MA (US); Kelly-Ann Schlegel, Fleetwood, PA (US); Yoheng Shu, Blue Bell, PA (US); Zhi-Qiang Yang, Schwenksville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 111 days.

(21) Appl. No.: 13/500,097

(22) PCT Filed: Oct. 25, 2010

(86) PCT No.: PCT/US2010/053908
§ 371 (c)(1), (2), (4) Date: Apr. 4, 2012

(87) PCT Pub. No.: WO2011/053542
PCT Pub. Date: May 5, 2011

(65) Prior Publication Data
US 2012/0202852 A1    Aug. 9, 2012

Related U.S. Application Data

(60) Provisional application No. 61/256,740, filed on Oct. 30, 2009.

(51) Int. Cl.
| | | |
|---|---|---|
| C07D 401/12 | (2006.01) |
| A61K 31/4439 | (2006.01) |
| C07D 401/06 | (2006.01) |
| C07D 233/64 | (2006.01) |
| C07D 249/04 | (2006.01) |
| C07D 257/04 | (2006.01) |
| C07D 271/10 | (2006.01) |
| C07D 277/28 | (2006.01) |
| C07D 413/04 | (2006.01) |
| C07D 413/06 | (2006.01) |
| C07D 417/14 | (2006.01) |
| C07D 263/32 | (2006.01) |

(52) U.S. Cl.
CPC ............ *C07D 401/06* (2013.01); *C07D 233/64* (2013.01); *C07D 249/04* (2013.01); *C07D 257/04* (2013.01); *C07D 271/10* (2013.01); *C07D 277/28* (2013.01); *C07D 413/04* (2013.01); *C07D 413/06* (2013.01); *C07D 417/14* (2013.01); *C07D 263/32* (2013.01)
USPC ...................................... 514/340; 546/268.4

(58) Field of Classification Search
CPC ........................ C07D 401/12; A61K 31/4439
USPC ............................... 546/268.4; 514/340
See application file for complete search history.

(56) References Cited

U.S. PATENT DOCUMENTS

| | | |
|---|---|---|
| 6,852,725 B1 | 2/2005 | Thurieau et al. |
| 7,875,636 B2 | 1/2011 | Barrow et al. |
| 2005/0239656 A1 | 10/2005 | Koyangi et al. |
| 2009/0275550 A1 | 11/2009 | Barrow et al. |
| 2010/0249176 A1 | 9/2010 | Barrow et al. |
| 2010/0261724 A1 | 10/2010 | Barrow et al. |
| 2011/0112064 A1 | 5/2011 | Barrow et al. |

FOREIGN PATENT DOCUMENTS

| | | |
|---|---|---|
| EP | 0685463 | 12/1995 |
| WO | WO9964401 | 12/1999 |
| WO | WO2007012079 | 10/2007 |
| WO | WO2009054984 | 10/2007 |
| WO | WO2009054982 | 4/2009 |
| WO | WO2009054983 | 4/2009 |

OTHER PUBLICATIONS

European Search Report/European Search Opinion in EP10827301.6, Mar. 13, 2013.
Harmon et al., "Synthesis of Arylpropanoic Acids From Optically active 2-(Ioodophenyl) Propanoic Acids", Tetrahedron Letters, vol. 34, 1993, pp. 5333-5336.
Guillard et al. "N-Acyltrifluoromethanesulfonamides as New Chemoselective Acylating Agents for Aliphatic and Aromatic Amines", Tetrahedron, vol. 62, 2008, pp. 5608-5616.
Raed et al, "Direct and Waste-Free Amidations and Cycloadditons by Organocatalytic Activation of Carboxylic Acids at Room Tempature" Angewandte Chemie, International Edition, vol. 47, 2008, pp. 2876-2879.
Ghislandi et al., "Configurational Relationships in Antiphologistic Hydratopic Acids", II Farmaco, vol. 37, 1982, pp. 81-93.
Lee et al., "NH4OH-Promoted Crystallization Induced Dynamic Resolution of N-(S)-(1-Phenylethyl)_[alpha]-Chloro-[alpha]-aryl Acetamides for Asymmetric Syntheses of [alpha]-mercapto Carboxylic Acid Derivatives", Synlett, vol. 2001, pp. 1941-1943.
Mandai et al., "An Efficient Synthesis of (2 S)-2-[4-((1 R, 2 S)-2-Hydroxycyclopentylmethyl)phenyl]propionic Acid", Synlett, vol. 2000, 2000, pp. 0862-0864.
Patani et al., "Bioisterism: A Rational Approach in Drug Design", Chemical Reviews, vol. 96, 1996, pp. 3147-3176.
Hupe et al., "The Inhibition of Receptor-mediated and Voltage Dependent Calcium Entry by the Antiproliferative L-651, 682", J. of Biological Chemistry, 1991, vol. 266, pp. 10136-10142.
Uebele et al., "Antagonism of T-Type Calcium Channels Inhibits High-Fat Diet-Induced Weight Gain in Mice", J. of Clinical Investigation, 2009, vol. 119, pp. 1659-1667.

*Primary Examiner* — Patricia L Morris
(74) *Attorney, Agent, or Firm* — J. Eric Thies; John C. Todaro

(57) ABSTRACT

The present invention is directed to heterocycle amide compounds which are antagonists of T-type calcium channels, and which are useful in the treatment or prevention of disorders and diseases in which T-type calcium channels are involved. The invention is also directed to pharmaceutical compositions comprising these compounds and the use of these compounds and compositions in the prevention or treatment of such diseases in which T-type calcium channels are involved.

9 Claims, No Drawings

HETEROCYCLE AMIDE T-TYPE CALCIUM CHANNEL ANTAGONISTS

CROSS REFERENCE TO RELATED APPLICATIONS

This application is a U.S. National Phase application under 35 U.S.C. §371 of PCT Application No. PCT/US2010/053908, filed Oct. 25, 2010, which claims priority under 35 U.S.C. §119(e) from U.S. Ser. No. 61/256,740 filed Oct. 30, 2009.

BACKGROUND OF THE INVENTION

Plasma membrane calcium channels are members of a diverse superfamily of voltage gated channel proteins. Calcium channels are membrane-spanning, multi-subunit proteins that allow controlled entry of Ca2+ ions into cells from the extracellular fluid. Excitable cells throughout the animal kingdom, and at least some bacterial, fungal and plant cells, possess one or more types of calcium channel. Nearly all "excitable" cells in animals, such as neurons of the central nervous system (CNS), peripheral nerve cells and muscle cells, including those of skeletal muscles, cardiac muscles, and venous and arterial smooth muscles, have voltage-dependent calcium channels.

Multiple types of calcium channels have been identified in mammalian cells from various tissues, including skeletal muscle, cardiac muscle, lung, smooth muscle and brain. A major type of this family are the L-type calcium channels, whose function is inhibited by the familiar classes of calcium channel blockers (dihydropyridines such as nifedipine, phenylalkylamines such as verapamil, and benzothiazepines such as diltiazem). Additional classes of plasma membrane calcium channels are referred to as T, N, P, Q and R.

The "T-type" (or "low voltage-activated") calcium channels are so named because their openings are of briefer duration (T=transient) than the longer (L=long-lasting) openings of the L-type calcium channels. The L, N, P and Q-type channels activate at more positive potentials (high voltage activated) and display diverse kinetics and voltage-dependent properties. There are three subtypes of T-type calcium channels that have been molecularly, pharmacologically, and electrophysiologically identified from various warm blooded animals including rat [J Biol. Chem. 276(6) 3999-4011 (2001); Eur J Neurosci 11(12):4171-8 (1999); reviewed in Cell Mol Life Sci 56(7-8):660-9 (1999)]. These subtypes have been termed α1G, α1H, and α1I. The molecular properties of these channels demonstrate that the amino acid sequences are between 60-70% identical. The electrophysiological characterization of these individual subtypes has revealed differences in their voltage-dependent activation, inactivation, deactivation and steady-state inactivation levels and their selectivities to various ions such as barium (J Biol. Chem. 276(6) 3999-4011 (2001)). Pharmacologically, these subtypes also have differing sensitivities to blockade by ionic nickel. These channel subtypes are also expressed in various forms due to their ability to undergo various splicing events during their assembly (J Biol. Chem. 276(6) 3999-4011 (2001)).

T-type calcium channels have been implicated in pathologies related to various diseases and disorders, including epilepsy, essential tremor, pain, neuropathic pain, schizophrenia, Parkinson's disease, depression, anxiety, sleep disorders, sleep disturbances, psychosis, schizophrenia, cardiac arrhythmia, hypertension, pain, cancer, diabetes, infertility and sexual dysfunction (J Neuroscience, 14, 5485 (1994); Drugs Future 30(6), 573-580 (2005); EMBO J, 24, 315-324 (2005); Drug Discovery Today, 11, 5/6, 245-253 (2006)). The known therapeutic regimens for such treating such diseases and disorders suffer from numerous problems. Accordingly, a more physiological way to treat these diseases and disorders would be highly desirable.

SUMMARY OF THE INVENTION

The present invention is directed to heterocycle amide compounds which are antagonists of T-type calcium channels, and which are useful in the treatment or prevention of neurological and psychiatric disorders and diseases in which T-type calcium channels are involved. The invention is also directed to pharmaceutical compositions comprising these compounds and the use of these compounds and compositions in the prevention or treatment of such diseases in which T-type calcium channels are involved.

DETAILED DESCRIPTION OF THE INVENTION

The present invention is directed to compounds of the formula I:

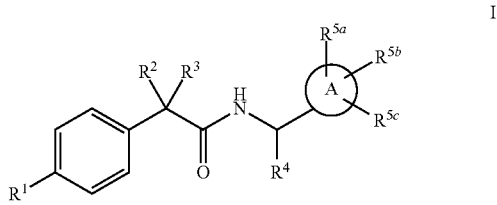

wherein:
A is phenyl or heterocycle;
$R^1$ is selected from the group consisting of:
  (1) $C_{1-6}$alkyl, which is unsubstituted or substituted with halo, $C_{3-6}$cycloalkyl or phenyl,
  (2) $C_{3-6}$cycloalkyl, which is unsubstituted or substituted with halo, $C_{3-6}$cycloalkyl or phenyl,
  (3) phenyl, which is unsubstituted or substituted with one or more substituents selected from $R^6$, and
  (4) heteroaryl, which is unsubstituted or substituted with one or more substituents selected from $R^6$;
$R^2$ and $R^3$ are independently selected from the group consisting of:
  (1) hydrogen,
  (2) halogen,
  (3) $C_{1-6}$alkyl, which is unsubstituted or substituted with halo, $C_{3-6}$cycloalkyl or phenyl, and
  (4) $C_{3-6}$cycloalkyl, which is unsubstituted or substituted with halo, $C_{3-6}$cycloalkyl or phenyl;
$R^4$ is selected from the group consisting of:
  (1) $C_{1-6}$alkyl, which is unsubstituted or substituted with one or more substituents selected from $R^6$,
  (2) $C_{2-6}$alkenyl, which is unsubstituted or substituted with one or more substituents selected from $R^6$,
  (3) —$C_{3-6}$cycloalkyl, which is unsubstituted or substituted with one or more substituents selected from $R^6$,
  (4) heteroaryl, which is unsubstituted or substituted with one or more substituents selected from $R^6$,
  with the proviso that if A is pyridyl, then $R^4$ is heteroaryl, which is unsubstituted or substituted with one or more substituents selected from $R^6$;
$R^{5a}$, $R^{5b}$ and $R^{5c}$ are independently selected from the group consisting of:

(1) hydrogen,
(2) halogen,
(3) hydroxyl,
(4) $C_{1-6}$alkyl, which is unsubstituted or substituted with halogen, hydroxyl, phenyl, —O—$C_{1-6}$alkyl, —O—(CO)$C_{1-6}$alkyl, or $C_{3-6}$cycloalkyl,
(5) —O—$C_{1-6}$alkyl, which is unsubstituted or substituted with halogen, hydroxyl, phenyl, —O—$C_{1-6}$alkyl, —O—(CO)$C_{1-6}$alkyl, or $C_{3-6}$cycloalkyl,
(6) —$C_{2-4}$alkenyl, and
(7) heteroaryl, which is unsubstituted or substituted with one or more substituents selected from $R^6$;

$R^6$ is selected from the group consisting of:
(1) hydroxyl,
(2) halogen,
(3) $C_{1-6}$alkyl, which is unsubstituted or substituted with halogen, hydroxyl-, phenyl, —O—$C_{1-6}$alkyl, —O—(CO)$C_{1-6}$alkyl, —(CO)—O—$C_{1-6}$alkyl, or $C_{3-6}$cycloalkyl,
(4) —$C_{3-6}$cycloalkyl, which is unsubstituted or substituted with halogen, hydroxyl, phenyl, —O—$C_{1-6}$alkyl, —O—(CO)$C_{1-6}$alkyl, or $C_{3-6}$cycloalkyl,
(5) —O—$C_{1-6}$alkyl,
(6) —O(C=O)—$C_{1-6}$alkyl,
(7) —NH—$C_{1-6}$alkyl,
(8) —$NH_2$,
(9) phenyl, which is unsubstituted or substituted with halogen, hydroxyl, phenyl, —O—$C_{1-6}$alkyl, —O—(CO)$C_{1-6}$alkyl, or $C_{3-6}$cycloalkyl,
(10) heterocycle, which is unsubstituted or substituted with halogen, hydroxyl, phenyl, —O—$C_{1-6}$alkyl, —O—(CO)$C_{1-6}$alkyl, or $C_{3-6}$cycloalkyl,
(11) —$CO_2H$, and
(12) —CN;

or a pharmaceutically acceptable salt thereof.

An embodiment of the present invention includes compounds of the formula Ia:

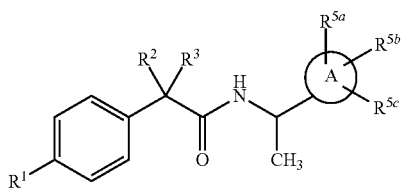

wherein A, $R^1$, $R^2$, $R^3$, $R^{5a}$, $R^{5b}$ and $R^{5c}$ are defined herein; or a pharmaceutically acceptable salt thereof.

An embodiment of the present invention includes compounds of the formula Ia':

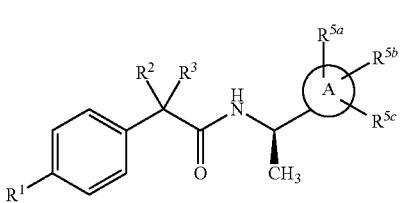

wherein A, $R^1$, $R^2$, $R^3$, $R^{5a}$, $R^{5b}$ and $R^{5c}$ are defined herein; or a pharmaceutically acceptable salt thereof.

An embodiment of the present invention includes compounds of the formula Ib:

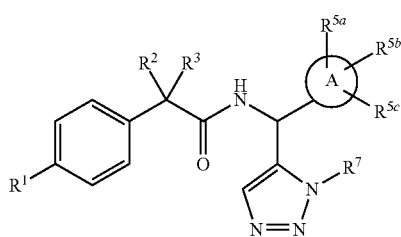

wherein A, $R^1$, $R^2$, $R^3$, $R^{5a}$, $R^{5b}$ and $R^{5c}$ are defined herein, and wherein $R^7$ is a substituent selected from the group consisting of:
(1) halogen,
(2) hydroxyl, and
(3) $C_{1-6}$alkyl, which is unsubstituted or substituted with halogen, hydroxyl, phenyl, —O—$C_{1-6}$alkyl, —O—(CO)$C_{1-6}$alkyl, or $C_{3-6}$cycloalkyl;

or a pharmaceutically acceptable salt thereof.

An embodiment of the present invention includes compounds of the formula Ib':

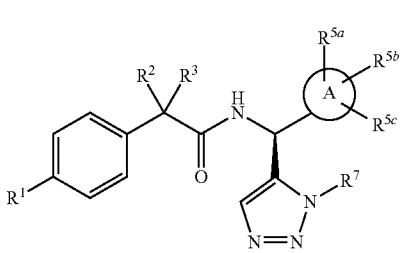

wherein A, $R^1$, $R^2$, $R^3$, $R^{5a}$, $R^{5b}$, $R^{5c}$, and $R^7$ are defined herein; or a pharmaceutically acceptable salt thereof.

An embodiment of the present invention includes compounds of the formula Ic:

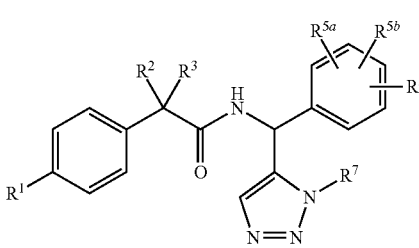

wherein A, $R^1$, $R^2$, $R^3$, $R^{5a}$, $R^{5b}$, $R^{5c}$, and $R^7$ are defined herein; or a pharmaceutically acceptable salt thereof.

An embodiment of the present invention includes compounds of the formula Ic':

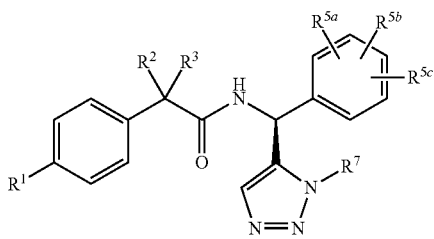

Ic' wherein A, $R^1$, $R^2$, $R^3$, $R^{5a}$, $R^{5b}$, $R^{5c}$, and $R^7$ are defined herein; or a pharmaceutically acceptable salt thereof.

An embodiment of the present invention includes compounds of the formula Id:

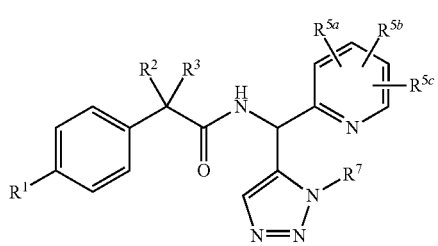

Id wherein A, $R^1$, $R^2$, $R^3$, $R^{5a}$, $R^{5b}$, $R^{5c}$, and $R^7$ are defined herein; or a pharmaceutically acceptable salt thereof.

An embodiment of the present invention includes compounds of the formula Id':

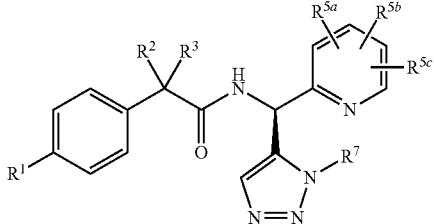

Id' wherein A, $R^1$, $R^2$, $R^3$, $R^{5a}$, $R^{5b}$, $R^{5c}$, and $R^7$ are defined herein; or a pharmaceutically acceptable salt thereof.

An embodiment of the present invention includes compounds of the formula Ie:

Ie

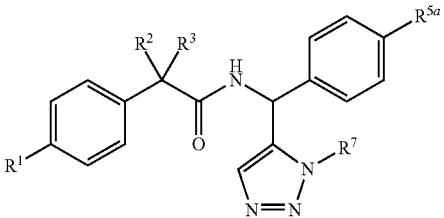

wherein A, $R^1$, $R^2$, $R^3$, $R^{5a}$, and $R^7$ are defined herein; or a pharmaceutically acceptable salt thereof.

An embodiment of the present invention includes compounds of the formula Ie':

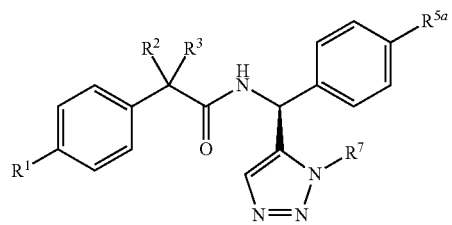

Ie' wherein A, $R^1$, $R^2$, $R^3$, $R^{5a}$, and $R^7$ are defined herein; or a pharmaceutically acceptable salt thereof.

An embodiment of the present invention includes compounds of the formula If:

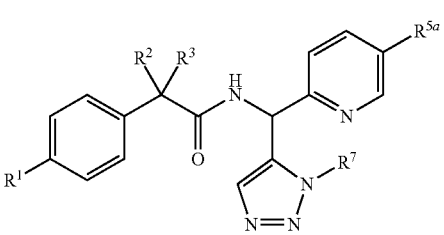

If wherein A, $R^1$, $R^2$, $R^3$, $R^{5a}$, and $R^7$ are defined herein; or a pharmaceutically acceptable salt thereof.

An embodiment of the present invention includes compounds of the formula If':

If' wherein A, $R^1$, $R^2$, $R^3$, $R^{5a}$, and $R^7$ are defined herein; or a pharmaceutically acceptable salt thereof.

An embodiment of the present invention includes compounds wherein A is selected from the group consisting of:
(1) phenyl,
(2) pyridyl,
(3) dihydroisoxazole,
(4) imidazopyrazine,
(5) imidazopyridazine,
(6) imidazopyridine,
(7) indazole,
(8) indole,
(9) naphthyridine,
(10) pyrazine,
(11) pyrazolopyrazine,
(12) pyrazolopyridazine,
(13) pyrazolopyrimidine,
(14) pyridine,
(15) pyrrolopyridine,
(16) pyrrolopyrimidine,
(17) quinazoline,
(18) quinoxaline,

(19) tetrahydrofuran,
(20) thiazole,
(21) triazole, and
(22) tetrazole.

Within this embodiment, the present invention includes compounds wherein A is selected from the group consisting of:
(1) phenyl,
(2) pyridyl,
(3) thiazole,
(4) triazole,
(5) oxadiazole,
(6) tetrahydrofuran, and
(7) tetrazole.

Within this embodiment, the present invention includes compounds wherein A is phenyl. Also within this embodiment, the present invention includes compounds wherein A is pyridyl. Also within this embodiment, the present invention includes compounds wherein A is thiazole. Also within this embodiment, the present invention includes compounds wherein A is oxadiazole. Also within this embodiment, the present invention includes compounds wherein A is triazole. Also within this embodiment, the present invention includes compounds wherein A is tetrahydrofuran. Also within this embodiment, the present invention includes compounds wherein A is tetrazole.

An embodiment of the present invention includes compounds wherein:
$R^1$ is selected from the group consisting of:
(1) $C_{1-6}$alkyl, and
(2) $C_{3-6}$cycloalkyl.

Within this embodiment, the present invention includes compounds wherein $R^1$ is selected from the group consisting of:
(1) isopropyl,
(2) tert-butyl, and
(2) cyclopropyl.

An embodiment of the present invention includes compounds wherein $R^2$ and $R^3$ are independently selected from the group consisting of:
(1) hydrogen,
(2) fluoro,
(3) $C_{1-6}$alkyl, which is unsubstituted or substituted with halogen or $C_{3-6}$cycloalkyl, and
(4) $C_{3-6}$cycloalkyl.

Within this embodiment, the present invention includes compounds wherein $R^2$ is hydrogen and $R^3$ is hydrogen. Within this embodiment, the present invention includes compounds wherein $R^2$ is fluoro and $R^3$ is fluoro. Within this embodiment, the present invention includes compounds wherein $R^2$ is methyl and $R^3$ is hydrogen. Within this embodiment, the present invention includes compounds wherein $R^2$ is cyclopropyl and $R^3$ is hydrogen.

Within this embodiment, the present invention includes compounds wherein $R^4$ is in the (R) orientation.

An embodiment of the present invention includes compounds wherein $R^4$ is selected from the group consisting of:
(1) $C_{1-6}$alkyl, which is unsubstituted or substituted with halogen, hydroxyl, —$C_{3-6}$cycloalkyl, or —O—$C_{1-6}$alkyl,
(2) —$C_{2-6}$alkenyl, and
(3) —$C_{3-6}$cycloalkyl.

Within this embodiment, the present invention includes compounds wherein $R^4$ is selected from the group consisting of:
(1) $CH_3$,
(2) $CH_2OH$,
(3) $CH_2OCH_3$,
(4) $CH_2CH_3$,
(5) $CH=CH_2$,
(6) $CH_2CH_2OH$,
(7) $CH_2CH=CH_2$,
(8) $CH_2CH_2F$,
(9) $CH_2CF_2$,
(10) $CH_2$-phenyl,
(12) $CH_2$-cyclopropyl,
(13) $CH_2$-cyclobutyl,
(14) cyclopropyl,
(15) cyclobutyl, and
(16) $CH_2CH_2CH_3$.

Within this embodiment, the present invention includes compounds wherein $R^4$ is $CH_3$, $CH_2CH_3$, $CH_2OH$, $CH_2CH_2OH$ or cyclopropyl.

Within this embodiment, the present invention includes compounds wherein $R^4$ is $CH_3$.

Within this embodiment, the present invention includes compounds wherein $R^4$ is (R)—$CH_3$.

An embodiment of the present invention includes compounds wherein $R^4$ is triazolyl, which is unsubstituted or substituted with one or more substitutents selected from the group consisting of:
(1) halogen,
(2) hydroxyl, and
(3) $C_{1-6}$alkyl, which is unsubstituted or substituted with halogen, hydroxyl, phenyl, —O—(CO)$C_{1-6}$alkyl, —O—(CO)$C_{1-6}$alkyl, or $C_{3-6}$cycloalkyl.

An embodiment of the present invention includes compounds wherein A is pyridyl and $R^4$ is triazolyl, which is unsubstituted or substituted with one or more substitutents selected from the group consisting of
(1) halogen,
(2) hydroxyl,
(3) $C_{1-6}$alkyl, which is unsubstituted or substituted with halogen, hydroxyl, phenyl, —O—$C_{1-6}$alkyl, —O—(CO)$C_{1-6}$alkyl, or $C_{3-6}$cycloalkyl.

An embodiment of the present invention includes compounds wherein $R^{5b}$ is hydrogen, $R^{5c}$ is hydrogen and $R^{5a}$ is —O—$C_{1-6}$alkyl, which is unsubstituted or substituted with halogen, hydroxyl, phenyl, or $C_{3-6}$cycloalkyl.

An embodiment of the present invention includes compounds wherein $R^{5b}$ is hydrogen, $R^{5c}$ is hydrogen and $R^{5a}$ is independently selected from the group consisting of:
(1) hydrogen,
(2) fluoro,
(3) chloro,
(4) bromo,
(5) hydroxyl,
(6) —$CH_3$,
(7) —$CH_2OH$,
(8) —$CH_2CH_3$,
(9) —$CH_2=CH_2$, and
(10) —$CH_2CH_2CH_3$.

An embodiment of the present invention includes compounds wherein $R^{5b}$ is hydrogen, $R^{5c}$ is hydrogen and $R^{5a}$ is independently selected from the group consisting of:
(1) hydrogen,
(2) —$OCH_3$,
(3) —$OCH_2F$,
(4) —$OCH_2$-cyclopropyl,
(5) —$OCH_2$-phenyl,
(6) —$OCH_2CH_3$,
(7) —$OCH_2CF_3$, and
(8) —$OCH_2CH_2CH_3$.

Within this embodiment, the present invention includes compounds wherein $R^{5b}$ is hydrogen, $R^{5c}$ is hydrogen and $R^{5a}$ is —$OCH_2CF_3$.

Within this embodiment, the present invention includes compounds wherein $R^{5a}$ is located at the 5-position of the pyridyl, $R^{5b}$ is hydrogen and $R^{5c}$ is hydrogen.

Specific embodiments of the present invention include a compound which is selected from the group consisting of the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-8}$alkyl specifically includes methyl, ethyl, n-propyl, iso-propyl, n-butyl, iso-butyl, tert-butyl, pentyl, and hexyl. Similarly, $C_{2-6}$alkenyl is defined to identify the group as having 2, 3, 4, 5 or 6 carbons which incorporates at least one double bond, which may be in a E- or a Z-arrangement. A group which is designated as being independently substituted with substituents may be independently substituted with multiple numbers of such substituents. The term "heterocycle" as used herein includes both unsaturated and saturated heterocyclic moieties, wherein the unsaturated heterocyclic moieties (i.e. "heteroaryl") include benzoimidazolyl, benzimidazolonyl, benzofuranyl, benzofurazanyl, benzopyrazolyl, benzotriazolyl, benzothiophenyl, benzoxazolyl, carbazolyl, carbolinyl, cinnolinyl, dihydroisoxazole, furanyl, imidazolyl, imidazopyridazine, imidazopyrazine, indolinyl, indolyl, indolizinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyrazinyl, pyrazolyl, pyridazinyl, pyridopyridazinyl, pyridopyrimidinyl, pyridopyrazinyl, pyridazinyl, pyridyl, pyrimidinyl, pyrazolyl, pyrazolopyridazinyl, pyrazolopyridinyl, pyrazolopyrimidinyl, pyrrolyl, pyrrolopyridazinyl, pyrrolopyridinyl, pyrrolopyrimidinyl, quinazolinyl, quinolyl, quinoxalinyl, tetrazolyl, tetrazolopyridyl, thiadiazolyl, thiazolyl, thienyl, triazolopyridazinyl, triazolopyridinyl, triazolopyrimidinyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof and S-oxides thereof.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Examples of isotopes suitable for inclusion in the compounds of the invention include isotopes of hydrogen such as $^{2}H$ and 3H, carbon such as $^{11}C$, $^{13}C$ and $^{14}C$, nitrogen such as $^{13}N$ and $^{15}N$, oxygen such as $^{15}O$, $^{17}O$ and $^{18}O$, phosphorus such as $^{32}P$, sulfur such as $^{35}S$, fluorine such as $^{18}F$, iodine such as $^{123}I$ and $^{125}I$, and chlorine such as $^{36}Cl$. Certain isotopically-labelled compounds of Formula I, for example those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection. Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labelled compounds of Formula I can generally be prepared by conventional techniques known to those skilled in the art or by processes analogous to those described in the accompanying Examples using appropriate isotopically-labelled reagents in place of the non-labelled reagent previously employed.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of antagonizing T-type calcium channel activity in a patient such as a mammal in need of such inhibition comprising the administration of an effective amount of the compound. The present invention is directed to the use of the compounds disclosed herein as antagonists of T-type calcium channels activity. In addition to primates, especially humans, a variety of other mammals can be treated according to the method of the present invention. The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for antagonizing T-type calcium channel activity or treating the disorders and diseases noted herein in humans and animals.

The subject treated in the present methods is generally a mammal, in particular, a human being, male or female. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder. The terms "administration of" and or "administering a" compound should be understood to mean providing a compound of the invention or a prodrug of a compound of the invention to the individual in need thereof.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as T-type calcium channel antagonists may be readily determined without undue experimentation by methodology well known in the art, including the "FLIPR $Ca^{2+}$ Flux Assay" and the "T-type Calcium ($Ca^{2+}$) Antagonist Voltage-Clamp Assay" [described by Xia, et al., Assay and Drug Development Tech., 1(5), 637-645 (2003)]. In a typical experiment ion channel function from HEK 293 cells expressing the T-type channel alpha-1G, H, or I (CaV 3.1, 3.2, 3.3) is recorded to determine the activity of compounds in blocking the calcium current mediated by the T-type channel alpha-1G, H, or I (CaV 3.1, 3.2, 3.3). In this T-type calcium ($Ca^{2+}$) antagonist voltage-clamp assay calcium currents are elicited from the resting state of the human alpha-1 G, H, or I (CaV 3.1, 3.2, 3.3) calcium channel as follows. Sequence information for T-type (Low-voltage activated) calcium channels are fully disclosed in e.g., U.S. Pat. Nos. 5,618,720, 5,686,241, 5,710,250, 5,726,035, 5,792,846, 5,846,757, 5,851,824, 5,874,236, 5,876,958, 6,013,474, 6,057,114, 6,096,514, WO 99/28342, and J. Neuroscience, 19(6):1912-1921 (1999). Cells expressing the T-type channels were grown in growth media which comprised: DMEM, 10% Tet-system approved FBS (Clontech Laboratories Inc.), 100 microgram/ml Penicillin/Streptomycin, 2 mM L-Glutamine, 150 microgram/ml Zeocin, 5 microgram/ml Blasticidin. T-channel expression was induced by exposing the cells to 2 mM Tetracycline for 24 hrs. Glass pipettes are pulled to a tip diameter of 1-2 micrometer on a pipette puller. The pipettes are filled with the intracellular solution and a chloridized silver wire is inserted along its length, which is then connected to the headstage of the voltage-clamp amplifier. Trypsinization buffer was 0.05% Trypsin, 0.53 mM EDTA. The extracellular recording solution consists of (mM): 130 mM NaCl, 4 mM KCl, 1 mM MgCl2, 2 mM CaCl2, 20 mM HEPES, 30 Glucose, pH 7.4. The internal solution consists of (mM): 125 CsCl, 10 TEA-Cl, 10 HEPES, 8 NaCl, 0.06 CaCl2, 0.6 EGTA, 4 ATP-Mg, 0.3 GTP; 135 mM CsMeSO3, 1 MgCl2, 10 CsCl, 5 EGTA, 10 HEPES, pH 7.4; or 135 mM CsCl, 2 MgCl2, 3 MgATP, 2 Na2ATP, 1 Na2GTP, 5 EGTA, 10 HEPES, pH 7.4. Upon insertion of the pipette tip into the bath, the series resistance is noted (acceptable range is between 1-4 megaohm). The junction potential between the pipette and bath solutions is zeroed on the amplifier. The cell is then patched, the patch broken, and, after compensation for series resistance (>=80%), the voltage protocol is applied while recording the whole cell Ca2+ current response. Voltage protocols: (1) –80 mV holding potential every 20 seconds pulse to –20 mV for 70 msec duration; the effectiveness of the drug in inhibiting the current mediated by the channel is measured directly from measuring the reduction in peak current amplitude initiated by the voltage shift from –80 mV to –20 mV; (2). –100 mV holding potential every 15 seconds pulse to –20 mV for 70 msec duration; the effectiveness of the drug in inhibiting the current mediated by the channel is measured directly from measuring the reduction in peak current amplitude initiated by the shift in potential from −100 mV to −20 mV. The difference in block at the two holding potentials was used to determine the effect of drug at differing levels of inactivation induced by the level of resting state potential of the cells. After obtaining control baseline calcium currents, extracellular solutions containing increasing concentrations of a test compound are washed on. Once steady state inhibition at a given compound concentration is reached, a higher concentration of compound is applied. % inhibition of the peak inward control Ca2+ current during the depolarizing step to −20 mV is plotted as a function of compound concentration.

The intrinsic T-type calcium channel antagonist activity of a compound which may be used in the present invention may be determined by these assays. In particular, the compounds of the following examples had activity in antagonizing the T-type calcium channel in the aforementioned assays, generally with an $IC_{50}$ of less than about 10 μM. Some of the compounds within the present invention had activity in antagonizing the T-type calcium channel in the aforementioned assays with an $IC_{50}$ of less than about 1 μM. Such a result is indicative of the intrinsic activity of the compounds in use as antagonists of T-type calcium channel activity.

With respect to other compounds disclosed in the art, the present compounds exhibit unexpected properties, such as with respect to duration of action and/or metabolism, such as increased metabolic stability, enhanced oral bioavailability or absorption, and/or decreased drug-drug interactions. For example, with respect to compounds disclosed in PCT Application WO 2007/120729 (published Oct. 25, 2007), the present compounds exhibit unexpected properties, such as having a shorter duration of action (e.g. half-life, t ½).

T-type calcium channels have been implicated in a wide range of biological functions. This has suggested a potential role for these receptors in a variety of disease processes in humans or other species. The compounds of the present invention have utility in treating, preventing, ameliorating, controlling or reducing the risk of a variety of neurological and psychiatric disorders associated with calcium channels, including one or more of the following conditions or diseases: movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, seizure disorders, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); heart disease, abnormal heart rhythms and arrythmias, myocardial infarction, congestive heart failure, coronary heart disease, sudden death, stroke, sexual and reproductive dysfunction, such as impaired fertility, infertility, diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function; enhancing memory; increasing memory retention; increasing trained performance; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; sleep disorders, sleep disturbances, including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing the amount of Delta sleep early in the sleep cycle, increasing REM sleep late in the sleep cycle; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, obstructive sleep apnea, wakefulness, nocturnal myoclonus, REM sleep interruptions, jet-lag, shift workers' sleep disturbances, dyssomnias, night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); attention deficit/hyperactivity disorder (ADHD); conduct disorder; migraine (including migraine headache); urinary incontinence; overactive bladder (OAB); urge urinary incontinence (UUI); lower urinary tract symptoms (LUTS); substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute pain, chronic pain, severe pain, intractable pain, inflammatory pain, chronic inflammatory pain, diabetic neuropathy, chronic neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Thus, in an embodiment the present invention provides methods for: treating, controlling, ameliorating or reducing the risk of epilepsy, including absence epilepsy; treating or controlling Parkinson's disease; treating essential tremor; treating or controlling pain, including neuropathic pain; enhancing the quality of sleep; augmenting sleep maintenance; increasing REM sleep; increasing slow wave sleep; decreasing fragmentation of sleep patterns; treating insomnia; enhancing cognition; increasing memory retention; treating or controlling depression; treating or controlling psychosis; or treating, controlling, ameliorating or reducing the risk of schizophrenia, in a mammalian patient in need thereof which comprises administering to the patient a therapeutically effective amount of the compound of the present invention. The subject compounds are further useful in a method for the prevention, treatment, control, amelioration, or reducation of risk of the diseases, disorders and conditions noted herein.

The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.0001 to 10 mg/kg. of body weight daily are administered to the patient, e.g., humans and elderly humans, to obtain effective antagonism of T-type calcium channel. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; in another embodiment about 1 mg to 100 mg per patient per day; and in another embodiment about 5 mg to 50 mg per patient per day; in yet another embodiment about 1 mg to 30 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is envisioned. However, the combination therapy may also includes therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is envisioned. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, including about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be employed in combination with an anti-seizure agent such as carbamazepine, clonazepam, divalproex, ethosuximide, felbamate, fosphenyloin, gabapentin, lamotrigine, levetiracetam, lorazepam, midazolam, oxcarbazepine, phenobarbital, phenyloin, primidone, tiagabine, topiramate, valproate, vigabatrin or zonisamide. In another embodiment, the subject compound may be employed in combination with acetophenazine, alentemol, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene, trifluoperazine or valproic acid.

In another embodiment, the compounds of the present invention may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl)hydrochloride, COMT inhibitors such as entacapone, MOA-B inhibitors, antioxidants, A2a adenosine receptor antagonists, cholinergic agonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the compounds of the present invention may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form.

In another embodiment, the compounds of the present invention may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine. In another embodiment, the subject compound may be employed in combination with an L-type calcium channel antagonist, such as amlodipine. In another embodiment, the subject compound may be employed in combination with an NK-1 receptor antagonists, a beta-3 agonist, a 5-alpha reductase-inhibitor (such as finasteride or dutasteride), a M3 muscarinic receptor antagonist (such as darifenacin, fesoterodine, oxybutynin, solifenacin, tolterodine or trosipium) or duloxetine.

In another embodiment, the compounds of the present invention may be administered in combination with compounds which are known in the art to be useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, other T-type calcium channel antagonists, triazolopyridines, and the like, such as: adinazolam, allobarbital, alonimid, alprazolam, amitriptyline, amobarbital, amoxapine, armodafnil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the compounds of the present invention may be employed in combination with an antidepressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-$HT_{1A}$ agonists or antagonists, especially 5-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the compounds of the present invention may be employed in combination with anti-Alzheimer's agents; beta-secretase inhibitors; gamma-secretase inhibitors; growth hormone secretagogues; recombinant growth hormone; HMG-CoA reductase inhibitors; NSAIDs including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine H3 antagonists; AMPA agonists; PDE IV inhibitors; $GABA_A$ inverse agonists; or neuronal nicotinic agonists.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; BuLi: butyl-lithium; Piv: pivaloyl; Ac: acetyl; THF: tetrahydrofuran; DMSO: dimethylsulfoxide; EDC: N-(3-Dimethylaminopropyl)-N'-ethylcarbodiimide; Boc: tert-butyloxy carbonyl; $Et_3N$: triethylamine; DCM: dichloromethane; DCE: dichloroethane; DME: dimethoxyethane; DEA: diethylamine; DAST: diethylaminosulfur trifluoride; EtMgBr: ethylamgnesium bromide; BSA: bovine serum albumin; TFA: trifluoracetic acid; DMF: N,N-dimethylformamide; $SOCl_2$: thionyl chloride; CDI: carbonyl diimidazole; rt: room temperature; HPLC: high performance liquid chromatography. The compounds of the present invention can be prepared in a variety of fashions.

In some cases the final product may be further modified, for example, by manipulation of substituents. These manipulations may include, but are not limited to, reduction, oxidation, organometallic cross-coupling, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATE 1

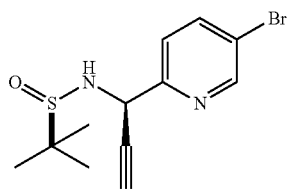

N-[(1R)-1-(5-bromopyridin-2-yl)prop-2-yn-1-yl]-(R)-2-methylpropane-2-sulfinamide To a solution of N-[(1E)-(5-bromopyridin-2-yl)methylene]-2-(R)-methylpropane-2-sulfinamide (4.06 g, 14.0 mmol) in dry $CH_2Cl_2$ (45 mL) at −78° C. was added ethynyl magnesiumbromide (34 mL, 0.5 Min THF). The reaction was stirred at −78° C. for 1 hour and then warm to room temperature for 1 hour. The reaction was quenched with sat. $NH_4Cl$ (40 mL). The reaction mixture was diluted with $CH_2Cl_2$ and the two layers were separated, and the water phase was extracted with EtOAc. The combined organic layers were dried with $Na_2SO_4$, filtered and concentrated. The residue was purified by silica flash chromatography (gradient, 5-65% EtOAc in hexanes) to give N-[(1R)-1-(5-bromopyridin-2-yl)prop-2-yn-1-yl]-(R)-2-methylpropane-2-sulfinamide as brown oil (3.2 g, 72%). ES-MS [M+1]+: 315.0. $^1$H NMR ($CDCl_3$, 400 MHz) δ 8.63 (d, J=2.4, 1H), 7.86 (dd, J=2.4, 8.8 Hz, 1H), 7.54 (d, J=8.8 Hz, 1H), 5.34 (dd, J=2.8, 4.4 Hz, 1H), 4.74 (d, J=4.0 Hz, 1H), 2.60 (d, J=2.4 Hz, 1H), 1.27 (s, 9H).

INTERMEDIATE 2

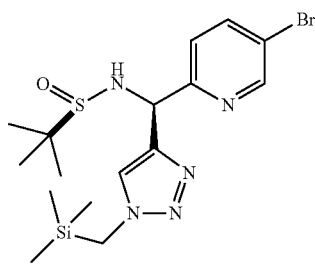 [SMILES: CC(C)(C)[S@@](=O)N[C@@H](c1ccc(Br)cn1)c1cn(C[Si](C)(C)C)nn1]

N-((S)-(5-bromopyridin-2-yl){1-[(trimethylsilyl)methyl]-1H-1,2,3-triazol-4-yl}methyl)-2-(R)-methylpropane-2-sulfinamide To a solution of N-[(1R)-1-(5-bromopyridin-2-yl)prop-2-yn-1-yl]-(R)-2-methylpropane-2-sulfinamide (2.0 g, 6.3 mmol) in a mixture t-BuOH (15 mL) and water (15 mL) was added (azidomethyl)(trimethyl)silane (0.94 mL, 6.3 mmol) followed by sodium ascorbate (0.63 mL, 1 M) and $CuSO_4$ (0.063 mL, 1 M). The reaction was stirred at room temperature for overnight. The reaction mixture was diluted with $H_2O$ and the product precipitated as a dark oily residue. The solvents were removed by decant. The residue was dissolved in $CH_2Cl_2$, dried with $Na_2SO_4$, filtered and concentrated. The residue was purified by silica flash chromatography (gradient, 5-100% EtOAc in hexanes) to give N-((S)-(5-bromopyridin-2-yl){1-[(trimethylsilyl)-methyl]-1H-1,2,3-triazol-4-yl}methyl)-2-(R)-methylpropane-2-sulfinamide (0.55 g, 19%). ES-MS [M+1]+: 446.0. $^1$H NMR ($CDCl_3$, 400 MHz) δ 8.59 (d, J=2.4 Hz, 1H), 7.80 (dd, J=2.4, 8.4, 1H), 7.41 (d, J=8.4 Hz, 1H), 7.34 (s, 1H), 5.83 (d, J=5.2, 1H), 5.35 (d, J=5.2 Hz, NH), 3.91-3.81 (m, 2H), 1.27 (s, 9H), 0.08 (s, 9H).

INTERMEDIATE 3

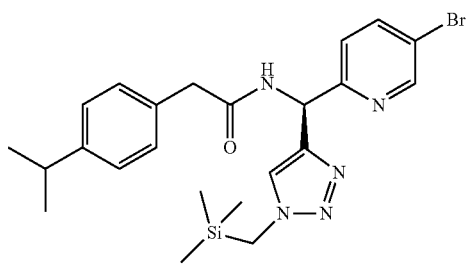 [SMILES: CC(C)c1ccc(CC(=O)N[C@@H](c2ccc(Br)cn2)c2cn(C[Si](C)(C)C)nn2)cc1]

N-((S)-(5-bromopyridin-2-yl){1-[(trimethylsilyl)methyl]-1H-1,2,3-triazol-4-yl}methyl)-2-(4-isopropylphenyl)acetamide To a solution of N-((S)-(5-bromopyridin-2-yl){1-[(trimethylsilyl)methyl]-1H-1,2,3-triazol-4-yl}methyl)-2-(R)-methylpropane-2-sulfinamide (0.61 g, 1.4 mmol) in MeOH (3 mL) was added a solution of HCl in ether (2.1 mL, 2 M). The reaction was stirred at room temperature for 1 h. The solvents were removed by concentration. The resulted amine was mixed with 4-isopropylpheylacetic acid (0.25 g, 1.4 mmol), HOAt (0.19 g, 1.4 mmol), EDC (0.26 g, 1.4 mmol) and diisopropylethyl amine (0.45 mL, 2.7 mmol) in CH$_2$Cl$_2$ (6.0 mL) and stirred at room temperature for 0.5 h. The solvent was removed and the residue was purified by silica flash chromatography (gradient, 5-75% EtOAc in hexanes) to give N-((S)-(5-bromopyridin-2-yl){1-[(trimethylsilyl)methyl]-1H-1,2,3-triazol-4-yl}methyl)-2-(4-isopropylphenyl)acetamide (0.40 g, 58%). ES-MS [M+1]$^+$: 502.1. $^1$H NMR (CDCl$_3$, 400 MHz) δ 8.53 (d, J=2.0 Hz, 1H), 7.75 (dd, J=2.4, 8.0 Hz, 1H), 7.38 (d, J=7.2 Hz, 1H), 7.32 (s, 1H), 7.25-7.18 (m, 4H), 6.25 (d, J=6.8 Hz, 1H), 3.79 (s, 2H), 3.62 (s, 2H), 2.90 (quintet, J=6.8 Hz, 1H), 2.50 (d, J=6.8 Hz, 6 H), 0.10 (s, 9H).

EXAMPLE 1

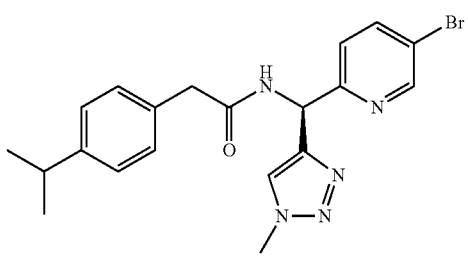 [SMILES: CC(C)c1ccc(CC(=O)N[C@@H](c2ccc(Br)cn2)c2cn(C)nn2)cc1]

N-[(S)-(5-bromopyridin-2-yl)(1-methyl-1,1-1,2,3-triazol-4-yl)methyl]-2-(4-isopropylphenyl)acetamide To a solution of N-((S)-(5-bromopyridin-2-yl){1-[(trimethylsilyl)methyl]-1H-1,2,3-triazol-4-yl}methyl)-2-(4-isopropylphenyl)acetamide (0.4 g, 0.80 mmol) in THF (5.0 mL) was added a solution of TBAF in THF (0.84 mL, 1 M). The reaction was stirred at room temperature for 1 h. The solvent was removed and the residue was purified by silica flash chromatography (gradient, 10-100% EtOAc in hexanes) to give N-[(S)-(5-bromopyridin-2-yl) (1-methyl-1H-1,2,3-triazol-4-yl)methyl]-2-(4-isopropylphenyl)acetamide (0.22 g, 65%). ES-MS [M+1]$^+$: 428.0. $^1$H NMR (CDCl$_3$, 400 MHz) δ 8.53 (d, J=2.0 Hz, 1H), 7.76 (dd, J=2.4, 8.0 Hz, 1H), 7.4w (s, 1H), 7.36 (d, J=6.8 Hz, 1H), 7.23 (d, J=8.0 Hz, 1H), 7.22 (s, 4H), 6.26 (d, J=6.8 Hz, 1H), 4.01 (s, 3H), 3.62 (s, 2H), 2.94-2.85 (m, J=6.8 Hz, 1H), 1.25 (d, J=7.2 Hz, 6H). HRMS (ES) [M+1]$^+$ calcd for C$_{20}$H$_{22}$BrN$_5$O: 428.1081. Found: 428.1112.

EXAMPLE 2

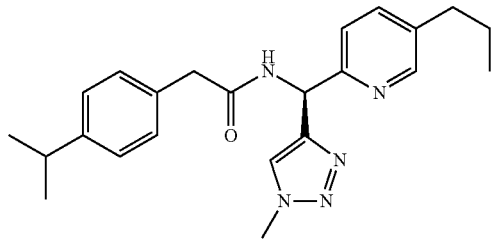 [SMILES: CCCc1ccc([C@H](NC(=O)Cc2ccc(C(C)C)cc2)c2cn(C)nn2)nc1]

2-(4-isopropylphenyl)-N-[(S)-(1-methyl-1H-1,2,3-triazol-4-yl)(5-propylpyridin-2-yl)methyl]acetamide N-[(S)-(5-bromopyridin-2-yl)(1-methyl-1H-1,2,3-triazol-4-yl)methyl]-2-(4-isopropylphenyl)acetamide (0.075 g, 0.18 mmol) was mixed with n-propylboronic acid (0.04 g, 0.44 mmol), PdCl$_2$(dppf)$_2$ (0.014 g, 0.019 mmol), Ag$_2$O (0.10 g, 0.44 mmol) and K$_2$CO$_3$ (0.073 g, 0.53 mmol) and degassed. THF (3 mL) was added and the mixture was heated in microwave at 130 C for 30 min. The reaction mixture was diluted with EtOAc and filtered through Celite. The solvent was removed and the residue was purified by reverse HPLC to give 2-(4-isopropylphenyl)-N-[(S)-(1-methyl-1H-1,2,3-triazol-4-yl)(5-propylpyridin-2-yl)methyl]acetamide (0.035 g, 51%). ES-MS [M+1]$^+$: 430.1. $^1$H NMR (CDCl$_3$, 400 MHz) δ $^1$H NMR (CDCl$_3$, 400 MHz) δ 8.29 (d, J=2.0 Hz, 1H), 7.58 (d, J=6.4 Hz, 1H), 7.45 (dd, J=2.4, 8.0 Hz, 1H), 7.40 (s, 1H), 7.27 (d, J=8.0 Hz, 1H), 7.24-7.19 (ABq, 4H), 6.27 (d, J=7.2 Hz, 1H), 3.98 (s, 3H), 3.62 (s, 2H), 2.94-2.85 (m, J=6.8 Hz, 1H), 2.54 (t, J=7.6 Hz, 2 H), 1.66-1.56 (m, 2H), 1.24 (d, J=6.4 Hz, 6H), 0.93 (t, J=7.2 Hz, 3H). HRMS (ES) [M+1]$^+$ calcd for C$_{23}$H$_{29}$N$_5$O: 392.2445. Found: 392.2446.

INTERMEDIATE 4

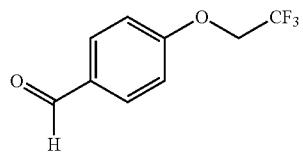 [SMILES: O=Cc1ccc(OCC(F)(F)F)cc1]

4-(2,2,2-trifluoroethoxy)benzaldehyde

To a solution of 4-hydroxyl benzaldehyde (1.1 g, 8.7 mmol) and Cs$_2$CO$_3$ (4.3 g, 13.1 mmol) in DMF (16 mL) was added 2,2,2-trifluoroethyl trifluoromethanesulfonate (1.5 mL, 10.5 mmol). The reaction mixture was stirred at rt for 1 h and then diluted with H$_2$O, followed by extraction with EtOAc. The combined organic layers were dried over Na$_2$SO$_4$, filtered and concentrated. The NMR of the crude product obtained (1.8 g, 100%) was clean. $^1$H NMR (CDCl$_3$, 400 MHz) δ 9.93 (s, 1H), 7.91-7.87 (m, 2H), 7.09-7.05 (m, 2H), 4.45 (q, J=8.0 Hz, 2H).

25

INTERMEDIATE 5

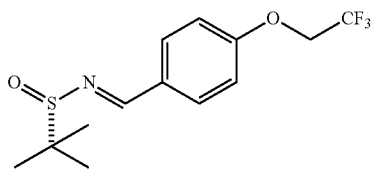 [SMILES: CC(C)(C)[S@](=O)/N=C/c1ccc(OCC(F)(F)F)cc1]

2-(S)-methyl-N-{[4-(2,2,2-trifluoroethoxy)phenyl]methylene}propane-2-sulfinamide To a solution of 4-(2,2,2-trifluoroethoxy)benzaldehyde (1.8 g, 8.7 mmol) and KHSO$_4$ (2.6 g, 19.6 mmol) in toluene (50 mL) was added (S)-t-butylsulfinamide (1.1 g, 8.7 mmol). The reaction mixture was stirred at 45° C. for overnight and then cooled and filtered through a Celite pad. The Celite pad was washed w/CH$_2$Cl$_2$. The combined solvents were removed by concentration. The residue was purified by silica gel flash chromatography (gradient, 0-25% EtOAc in hexanes) to give the product (1.3 g, 50%). ES-MS [M+1]$^+$: 308.0. $^1$H NMR (CDCl$_3$, 400 MHz) δ 8.53 (s, 1H), 7.86-7.83 (m, 2H), 7.04-7.01 (m, 2H), 4.42 (q, J=8.0 Hz, 2H), 1.26 (s, 9H).

INTERMEDIATE 6

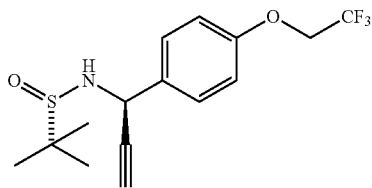 [SMILES: C#C[C@@H](N[S@@](=O)C(C)(C)C)c1ccc(OCC(F)(F)F)cc1]

2-(S)-methyl-N-{(1R)-1-[4-(2,2,2-trifluoroethoxy)phenyl]prop-2-yn-1-yl}propane-2-sulfinamide To a solution of 2-(S)-methyl-N-{[4-(2,2,2 trifluoroethoxy)phenyl]methylene}propane-2-sulfinamide (1.1 g, 3.6 mmol) in dry CH$_2$Cl$_2$ (15 mL) at −78° C. was added ethynyl magnesiumbromide (13 mL, 0.5 M in THF). The reaction was stirred at −78° C. for 10 min. and then warm to room temperature for overnight. The reaction was not completed. Another batch of ethynyl magnesiumbromide (13 mL, 0.5 M in THF) was added at −78° C. followed by stirring at rt overnight. The reaction was quenched with sat. NH$_4$Cl (10 mL). The reaction mixture was extracted with EtOAc. The combined organic layers were dried with Na$_2$SO$_4$, filtered and concentrated. The residue was purified by silica flash chromatography (gradient, 5-80% EtOAc in hexanes) to give the product (0.20 g, 17%). ES-MS [M+1]$^+$: 334.1. $^1$H NMR (CDCl$_3$, 400 MHz) δ 7.52-7.26 (m, 2H), 6.98-6.93 (m, 2H), 5.20 (dd, J=2.4, 6.0 Hz, 1H), 4.36 (q, J=8.0 Hz, 1H), 3.66 (d, J=6.0 Hz, 1H), 2.63 (d, J=2.4 Hz, 1H), 1.22 (s, 9H).

26

INTERMEDIATE 7

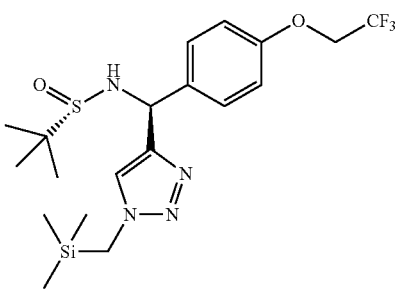 [SMILES: CC(C)(C)[S@](=O)N[C@@H](c1ccc(OCC(F)(F)F)cc1)c1cn(C[Si](C)(C)C)nn1]

2-(S)-methyl-N-((S)-[4-(2,2,2-trifluoroethoxy)phenyl]{1-[(trimethylsilyl)methyl]-1H-1,2,3-triazol-4-yl}methyl)propane-2-sulfinamide To a solution of 2-methyl-N-{(1R)-1-[4-(2,2,2-trifluoroethoxy)phenyl]prop-2-yn-1-yl}propane-2-sulfinamide (0.23 g, 0.70 mmol) in a mixture t-BuOH (1 mL) and water (1 mL) was added (azidomethyl)(trimethyl)silane (0.10 mL, 0.70 mmol) followed by sodium ascorbate (0.07 mL, 1 M) and CuSO$_4$ (0.007 mL, 1M). The reaction was stirred at room temperature for overnight. The reaction mixture was diluted with H$_2$O and the product precipitated as a dark oily residue. The solvents were removed by decant. The residue was dissolved in EtOAc, dried with Na$_2$SO$_4$, filtered and concentrated. The residue was purified by preparative thin layer chromatography (4:1 EtOAc/hexanes) to give the product (0.11 g, 33%). ES-MS [M+1]$^+$: 463.1. $^1$H NMR (CDCl$_3$, 400 MHz) δ 7.28-7.24 (m, 2H), 6.83-6.80 (m, 2H), 5.56 (d, J=2.4, 1H), 4.47 (d, J=2.4, 1H), 4.36 (q, J=8.0 Hz, 2H), 3.74-3.65 (m, 2H), 1.11 (s, 9H), 1.00 (s, 9H).

INTERMEDIATE 8

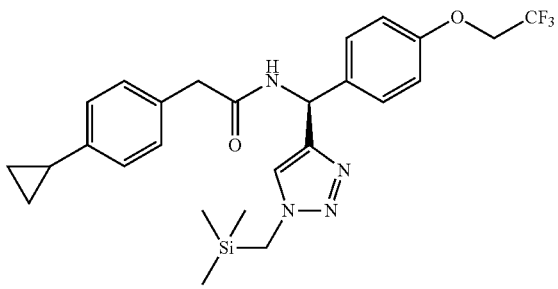 [SMILES: C[Si](C)(C)Cn1cc([C@@H](NC(=O)Cc2ccc(C3CC3)cc2)c2ccc(OCC(F)(F)F)cc2)nn1]

2-(4-cyclopropylphenyl)-N-((S)-[4(2,2,2-trifluoroethoxy)phenyl]{1[(trimethylsilyl)methyl]-1H-1,2,3-triazol-4-yl}methyl)acetamide To a solution of 2-(S)-methyl-N-((S)-[4-(2,2,2-trifluoroethoxy)phenyl]{1-[(trimethylsilyl)methyl]-1,1-1,2,3-triazol-4-yl}methyl)propane-2-sulfinamide (0.11 g, 0.23 mmol) in MeOH (1 mL) was added a solution of HCl in ether (0.45 mL, 2 M). The reaction was stirred at room temperature for 1.5 h. The solvents were removed by concentration. The resulted amine was mixed with 4-cyclopropylpheylacetic acid (0.040 g, 0.23 mmol), HOAt (0.034 g, 0.25 mmol), EDC (0.048 g, 0.25 mmol) and di-isopropylethyl amine (0.075 mL, 0.45 mmol) in DMF (1.0 mL) and stirred at room temperature for 1 h. The solvent was removed and the residue was purified by reverse-phase HPLC to give the product (0.070 g, 60%). $^1$H NMR (CDCl$_3$, 400 MHz) δ 7.15 (s, 1H), 7.11 (d, J=8.4 Hz, 1H), 7.01 (t, J=4.0 Hz, 2H), 6.90 (d, J=8.0 Hz, 2H), 6.73 (d, J=8.8 Hz, 1H), 6.75 (d, J=7.6 Hz, 1H), 6.10 (d, J=7.6 Hz, 1H), 4.19 (q, J=8.0 Hz, 1H), 3.75-3.67 (m, 2H), 3.43 (s, 2H), 1.78-1.72 (m, 1H), 0.86-0.81 (m, 2H), 0.57-0.53 (m, 2H), 0.00 (s, 9H). HRMS (ES) [M+1]$^+$ calcd for C$_{26}$H$_{31}$F$_3$N$_4$O$_2$Si: 517.2241. Found: 517.2272.

EXAMPLE 3

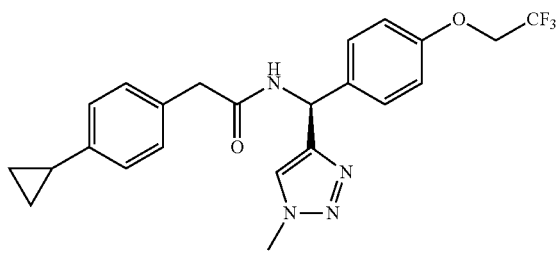 [SMILES: Cn1cc([C@@H](NC(=O)Cc2ccc(C3CC3)cc2)c2ccc(OCC(F)(F)F)cc2)nn1]

2-(4-cyclopropylphenyl)-N-{(S)-(1-methyl-1H-1,2,3-triazol-4-yl)[4-(2,2,2-ttrifluoroethoxy)phenyl]methyl}acetamide To a solution of 2-(4-cyclopropylphenyl)-N-((S)-[4(2,2,2-trifluoroethoxy)phenyl]{1[(trimethylsilyl)methyl]-1H-1,2,3-triazol-4-yl}methyl)acetamide (0.065 g, 0.13 mmol) in THF (0.5 mL) was added a solution of TBAF in THF (0.14 mL, 1 M). The reaction was stirred at room temperature for 0.5 h. The solvent was removed and the residue was purified by reverse-phase HPLC to give the product as white solid. $^1$H NMR (CDCl$_3$, 400 MHz) δ 7.22 (d, J=8.8 Hz, 1H), 7.13 (d, J=8.0 Hz, 1H), 7.02 (d, J=8.0 Hz, 1H), 6.85 (d, J=8.8 Hz, 1H), 6.76 (d, J=7.6 Hz, 1H), 6.23 (d, J=7.6 Hz, 1H), J=8.0 Hz, 2H), 4.03 (s, 3H), 3.66 (s, 2H), 1.90-1.84 (m, 1H), 0.97-0.93 (m, 2H), 0.69-0.65 (m, 2H). HRMS (ES) [M+1]$^+$ calcd for C$_{23}$H$_{23}$F$_3$N$_4$O$_2$: 445.1846. Found: 445.1861.

INTERMEDIATE 9

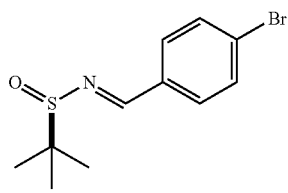

N-[(1E)-(4-bromophenyl)methylidene]-2-methylpropane-2-sulfinamide

To a solution of 2.0 g (10 mmol) 4-bromobenzaldehyde in 20 ml CH$_2$Cl$_2$ at rt was added 1.3 g (10 mmol) (S)-(−)-2-methylpropane-2-sulfinamide and 2.4 g (10 mmol) copper (II) sulfate. After 24 h at room temperature, the reaction mixture was filtered through celite and concentrated in vacuo. Purification by flash chromatography (silica gel, linear gradient 0-40% EtOAc:hexane) afforded 2.8 g (90%) N-[(1E)-(4-bromophenyl)methylidene]-2-methylpropane-2-sulfinamide. ES-MS [M+1]=289.0.

INTERMEDIATE 10

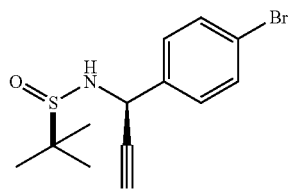 [SMILES: C#C[C@@H](N[S@](=O)C(C)(C)C)c1ccc(Br)cc1]

N-[(1R)-1-(4-bromophenyl)prop-2-ynyl]-2-methylpropane-2-sulfinamide

To a solution of 2.8 g (9.7 mmol) N-[(1E)-(4-bromophenyl)methylidene]-2-methylpropane-2-sulfinamide in 30 ml CH$_2$Cl$_2$ at −78° C. was added 49 mL (24 mmol) 0.5M bromo (ethynyl)magnesium in THF. The reaction mixture was warmed slowly to room temperature. After 24 h at room temperature, the reaction mixture was quenched with saturated ammonium chloride, extracted three times with methylene chloride, and washed with brine. The organic layer was dried over NaSO$_4$, filtered and concentrated in vacuo. Purification by flash chromatography (silica gel, linear gradient 0-100% EtOAc:hexane) afforded N-[(1R)-1-(4-bromophenyl)prop-2-ynyl]-2-methylpropane-2-sulfinamide. $^1$H NMR (CDCl$_3$, 400 MHz) 7.52-7.45 (m, 2H); 7.41-7.38 (m, 2H); 5.19 (dd, 1H, J=2.38 Hz, 6.05 Hz); 3.66 (br d, 1H, J=6.04 Hz); 2.64 (d, 1H, J=2.38 Hz); 1.20 (s, 9H). ESMS+1=316.0.

INTERMEDIATE 11

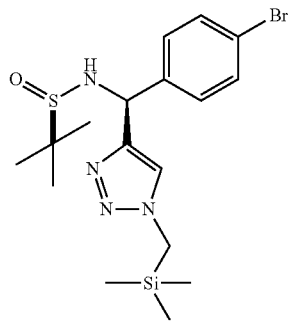 [SMILES: CC(C)(C)[S@@](=O)N[C@@H](c1ccc(Br)cc1)c1cn(C[Si](C)(C)C)nn1]

N-((S)-(4-bromophenyl){1-[(trimethylsilyl)methyl]-1H-1,2,3-triazol-4-yl}methyl)-2-methylpropane-2-sulfinamide To a solution of 1.5 g (4.8 mmol) N-[(1R)-1-(4-bromophenyl)prop-2-ynyl]-2-methylpropane-2-sulfinamide in 10 mL water and 10 mL t-butanol was added 0.62 g (azidomethyl) (trimethyl)silane, 0.48 mL (0.48 mmol) 1.0M aqueous ascorbic acid solution, and 0.05 mL (0.05 mmol) 1.0M solution of aqueous copper (II) sulfate pentahydrate. After 24 h at room temperature, the reaction mixture was quenched with water, extracted three times with ethyl acetate, and washed with brine. The organic layer was dried over Na₂SO₄, filtered and concentrated in vacuo. Purification by flash chromatography (silica gel, linear gradient 25-100% EtOAc:hexane) afforded N-((S)-(4-bromophenyl){1-[(trimethylsilyl)methyl]-1H-1,2,3-triazol-4-yl}methyl)-2-methylpropane-2-sulfinamide. ¹H NMR (CDCl₃, 400 MHz) 7.51-7.47 (m, 2H); 7.35-7.30 (m, 2H); 7.06 (s, 1H); 5.68 (d, 1H, J=2.65 Hz); 4.58 (d, 1H, J=2.48 Hz); 3.81 (d, 2H, J=3.84 Hz); 1.24 (s, 9H); 0.12 (s, 9H). ES-MS [M+1]⁺=444.94.

INTERMEDIATE 12

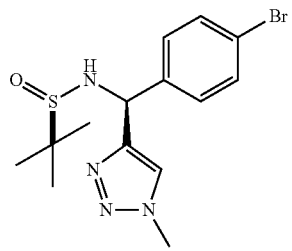 [SMILES: Cn1cc([C@@H](N[S@](=O)C(C)(C)C)c2ccc(Br)cc2)nn1]

N-[(S)-(4-bromophenyl)(1-methyl-1H-1,2,3-triazol-4-yl)methyl]-2-methylpropane-2-sulfinamide To a solution of 1.0 g (2.3 mmol) N-((S)-(4-bromophenyl){1-[(trimethylsilyl)-methyl]-1H-1,2,3-triazol-4-yl}methyl)-2-methylpropane-2-sulfinamide in 5.0 ml THF was added 2.5 mL (2.5 mmol) 1.0M solution TBAF. After 30 min at room temperature, the reaction mixture was concentrated in vacuo. Purification by flash chromatography (silica gel, linear gradient 0-10% MeOH:Methylene chloride) afforded 0.80 g (95%) N-[(S)-(4-bromophenyl)(1-methyl-1H-1,2,3-triazol-4-yl)methyl]-2-methylpropane-2-sulfinamide. ¹H NMR (CDCl₃, 400 MHz) 7.51-7.49 (m, 2H); 7.31 (m, 2H); 7.21 (s, 1H); 5.70 (d, 1H, J=2.96 Hz); 4.49 (d, 1H, J=2.75 Hz); 4.04 (s, 3H); 1.24 (s, 9H). ESMS [M+1]⁺=373.0.

INTERMEDIATE 13

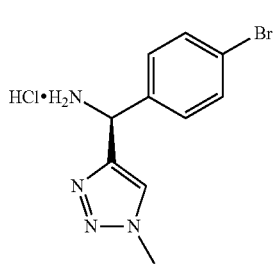

(S)-(4-bromophenyl)(1-methyl-1H-1,2,3-triazol-4-yl)methanaminium chloride

To a solution of 0.71 g (1.9 mmol) N-[(S)-(4-bromophenyl)(1-methyl-1H-1,2,3-triazol-4-yl)methyl]-2-methylpropane-2-sulfinamide in 5.0 ml MeOH was added 1.4 mL (2.8 mmol) 2.0M HCl in diethyl ether. After 30 min at room temperature, the reaction mixture was concentrated in vacuo to afford (S)-(4-bromophenyl)(1-methyl-1H-1,2,3-triazol-4-yl)methanaminium chloride. ES-MS [M+1]⁺=269.0.

EXAMPLE 4

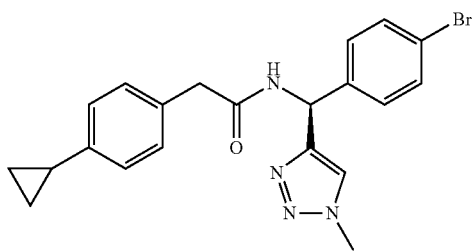 [SMILES: Cn1cc([C@@H](NC(=O)Cc2ccc(C3CC3)cc2)c2ccc(Br)cc2)nn1]

N-[(S)-(4-bromophenyl)(1-methyl-1H-1,2,3-triazol-4-yl)methyl]-2-(4-cyclopropylphenyl)acetamide To a solution of 0.075 g (0.426 mmol) (4-cyclopropylphenyl)acetic acid in 0.850 ml DMF was added 0.194 g (0.638 mmol) (S)-(4-bromophenyl)(1-methyl-1H-1,2,3-triazol-4-yl)methanaminium chloride 0.063 g (0.468 mmol) HOAT, 0.090 g (0.468 mmol) EDC, and 0.186 mL (1.06 mmol) triethylamine. After 24 hr at room temperature, the reaction mixture was purified by preparative HPLC (5->95% CH₃CN/H₂O over 15 min, 0.05% added TFA, C18) to afford 0.160 g (88%) N-[(S)-(4-bromophenyl)(1-methyl-1H-1,2,3-triazol-4-yl)methyl]-2-(4-cyclopropylphenyl)acetamide. ¹H NMR (CDCl₃, 400 MHz) 7.43-7.40 (m, 2H); 7.39 (m, 1H); 7.14 (m, 4H); 7.03 (d, 2H, J=8.25 Hz); 6.73 (d, 1H, J=7.41 Hz); 6.20 (d, 1H, J=7.50 Hz); 4.04 (s, 3H); 3.56 (s, 2H); 1.91-1.84 (m, 1H); 0.98-0.94 (m, 2H); 0.70-0.66 (m, 2H). HRMS (ES) [M+1]⁺ calcd for C₂₁H₂₁BrN₄O: 425.0977. Found: 425.0979.

EXAMPLE 15

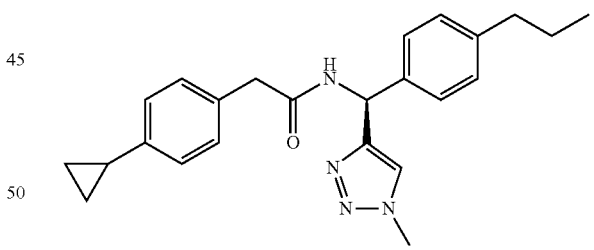

2-(4-cyclopropylphenyl)-N-[(S)-(1-methyl-1H-1,2,3-triazol-4-yl)(4-propylphenyl)methyl]acetamide To a solution of 0.086 g (0.202 mmol) N-[(S)-(4-bromophenyl)(1-methyl-1H-1,2,3-triazol-4-yl)methyl]-2-(4-cyclopropylphenyl)acetamide in 1.0 ml THF was added 0.021 g (0.243 mmol) n-propylboronic acid, 0.017 g (0.020 mmol) PdCl₂(dppf)-CH₂Cl₂ adduct, 0.084 g (0.607 mmol) solid potassium carbonate, and 0.117 g (0.607 mmol) Silver (I) oxide. The reaction mixture was irradiated in the microwave at 150° C. for 30 mins. The resulting solution was diluted with CH₂Cl₂, washed twice with water, dried over sodium sulfate, filtered, and concentrated in vacuo. Purification by preparative HPLC (5->95% CH₃CN/H₂O over 15 min, 0.05% added TFA, C18) to afford 0.024 g (30.6%) 2-(4-cyclopropylphenyl)-N-[(S)-(1-methyl-1H-1,2,3-triazol-4-yl)(4-propylphenyl)methyl]acetamide. ¹H NMR (CDCl₃, 400 MHz) 7.25 (m, 1H); 7.17-7.02 (m, 8H); 6.68 (d, J=8.24 Hz, 1H); 6.25 (d, J=7.78 Hz, 1H); 4.03 (s, 3H); 3.56 (s, 2H); 2.54 (t, J=7.42 Hz, 2H); 1.90-1.84 (m, 1H); 1.65-1.55-(m, 2H); 0.97-0.90 (m, 5H); 0.69-0.65 (m, 2H). HRMS (ES) [M+1]⁺ calcd for C₂₄H₂₈N₄O: 389.2341. Found: 389.2343.

INTERMEDIATE 14

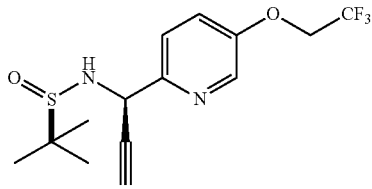 [SMILES: C#C[C@@H](N[S@](=O)C(C)(C)C)c1ccc(OCC(F)(F)F)cn1]

2-(R)-methyl-N-{(1R)-1-[5-(2,2,2-trifluoroethoxy)pyridin-2-yl]prop-2-yn-1-yl}propane-2-sulfinamide To a solution of 2-(R)-methyl-N-{[5-(2,2,2-trifluoroethoxy)pyridin-2-yl]methylidene}propane-2-sulfinamide (2.0 g, 6.5 mmol) in dry CH₂Cl₂ (20 mL) at −78° C. was added ethynyl magnesiumbromide (16 mL, 0.5 M in THF). The reaction was stirred at −78° C. for 1 h. and then warm to room temperature for 2 h. The reaction was not completed. Another batch of ethynyl magnesiumbromide (10 mL, 0.5 M in THF) was added at −78° C. followed by stirring at rt for 0.5 h. The reaction was quenched by sat. NH₄Cl (20 mL) and diluted with CH₂Cl₂. The two layers were separated, and the aqueous layer was extracted with EtOAc. The combined organic layers were dried with Na₂SO₄, filtered and concentrated. The residue was purified by silica flash chromatography (gradient, 5-65% EtOAc in hexanes) to give the product as a brown oil (1.3 g, 60%). ES-MS [M+1]⁺: 335.0. ¹H NMR (CDCl₃, 400 MHz) δ 8.32 (d, J=3.2 Hz, 1H), 7.60 (d, J=8.8 Hz, 1H), 7.31 (dd, J=2.8, 8.4 Hz, 1H), 5.36 (dd, J=2.4, 4.4 Hz, 1H), 4.71 (d, J=4.4 Hz, 1H), 4.41 (q, J=8.0 Hz, 1H), 2.59 (d, J=2.4 Hz, 1H), 1.27 (s, 9H).

INTERMEDIATE 15

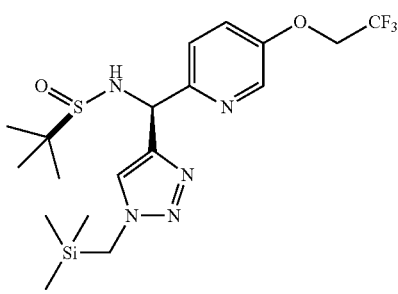 [SMILES: CC(C)(C)[S@@](=O)N[C@@H](c1ccc(OCC(F)(F)F)cn1)c1cn(C[Si](C)(C)C)nn1]

2-methyl-N-[(S)-[5-(2,2,2-trifluoroethoxy)pyridin-2-yl]{1-[(trimethylsilyl)methyl]-1H-1,2,3-triazol-4-yl}methyl]propane-2-sulfinamide To a solution of 2-(R)-methyl-N-{(1R)-1-[5-(2,2,2-trifluoroethoxy)pyridin-2-yl]prop-2-yn-1-yl}propane-2-sulfinamide (1.3 g, 3.9 mmol) in a mixture t-BuOH (10 mL) and water (10 mL) was added (azidomethyl)(trimethyl)silane (0.58 mL, 3.9 mmol) followed by sodium ascorbate (0.39 mL, 1 M) and CuSO₄ (0.039 mL, 1M). The reaction was stirred at room temperature for overnight. The reaction mixture was diluted with H₂O and the product precipitated as a dark oily residue. The solvents were removed by decant. The residue was dissolved in EtOAc, dried with Na₂SO₄, filtered and concentrated. The residue was purified by silica gel flash chromatography (30-100 EtOAc/hexanes) to give the product (1.3 g, 72%). ES-MS [M+1]⁺: 464.1. ¹H NMR (CDCl₃, 400 MHz) δ 8.28 (d, J=2.8 Hz; 1H), 7.47 (d, J=8.8 Hz, 1H), 7.34 (s, 1H), 7.24 (dd, J=2.8, 8.8 Hz, 1H), 5.84 (d, J=5.2 Hz, 1H), 5.34 (d, J=5.2 Hz, 1H), 4.38 (q, J=7.6 Hz, 2H), 3.86 (ABq, J=15.2, 23.6 Hz, 2H), 1.27 (s, 9H), 0.12 (s, 9H).

EXAMPLE 6

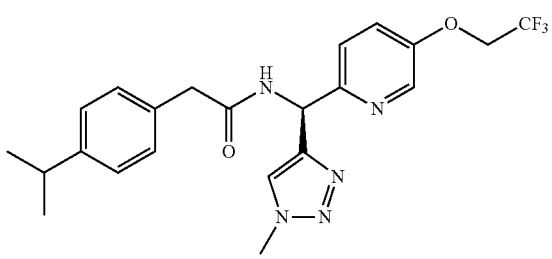 [SMILES: CC(C)c1ccc(CC(=O)N[C@@H](c2ccc(OCC(F)(F)F)cn2)c2cn(C)nn2)cc1]

2-(4-isopropylphenyl)-N-{(S)-(1-methyl-1H-1,2,3-triazol-4-yl)[4-(2,2,2-trifluoroethoxy)-phenyl]methyl}acetamide To a solution of 2-methyl-N-[(S)-[5-(2,2,2-trifluoroethoxy)pyridin-2-yl]{1-[(trimethylsilyl)methyl]-1H-1,2,3-triazol-4-yl}methyl]propane-2-sulfinamide (1.3 g, 2.8 mmol) in MeOH (6.3 mL) was added a solution of HCl in ether (6.3 mL, 2 M). The reaction was stirred at room temperature for 1 h. The solvents were removed by concentration. The resulted amine bis-HCl salt (0.3 g, 0.69 mmol) was mixed with 4-isopropylpheylacetic acid (0.12 g, 0.69 mmol), HOAt (0.094 g, 0.69 mmol), EDC (0.13 g, 0.69 mmol) and diisopropylethyl amine (0.23 mL, 1.4 mmol) in CH₂Cl₂ (3.5 mL) and stirred at room temperature for 0.5 h. The solvent was removed and the residue was purified by silica gel flash chromatography (30-100% EtOAc in Hex) to give the amide product. To a solution of this amide (0.23 g, 0.45 mmol) in THF (3 mL) was added a solution of TBAF (0.5 mL, 1M in THF). The reaction mixture was stirred at rt for 1 h. The solvent was removed and the residue was purified by silica gel flash chromatography (50-100% EtOAc in hex) to provide 2-(4-isopropylphenyl)-N-{(S)-1-methyl-1H-1,2,3-triazol-4-yl)[4-(2,2,2-trifluoroethoxy)-phenyl]methyl}acetamide (0.12 g, 59%). ¹H NMR (CDCl₃, 400 MHz) δ 8.22 (d, J=2.8 Hz, 1H), 7.40 (s, 1H), 7.39 (d, J=7.2 Hz, 1H), 7.33 (d, J=8.8 Hz, 1H), 7.24-7.19 (m, 5H), 6.27 (d, J=6.8 Hz, 1H), 4.31 (dd, J=7.6, 8.4 Hz, 2H), 4.00 (s, 3H), 3.62 (s, 2H), 2.90 (m, J=6.8 Hz, 1H), 1.25 (d, J=6.8 Hz, 6H). HRMS (ES) [M+1]⁺ calcd for C₂₂H₂₄F₃N₅O₂: 448.1955, Found: 448.1956.

INTERMEDIATE 16

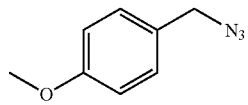

1-(azidomethyl)-4-methoxybenzene

To a solution of p-methoxybenzyl chloride (4.26 mL, 31.4 mmol) in DMF (20 mL) was added sodium azide (2.04 g, 31.4 mmol). The reaction mixture was stirred at room temperature for 48 hours, diluted with H$_2$O (200 mL), and then extracted with ether. The combined organic layers were washed w/H$_2$O, dried over Na$_2$SO$_4$, filtered and conc. The clear oil obtained (4.9 g, 96%) was pure enough to use. $^1$H NMR (CDCl$_3$, 400 MHz) 7.26-7.23 (m, 2H); 6.93-6.89 (m, H); 4.27 (s, 2H); 3.82 (s, 3H).

INTERMEDIATE 17

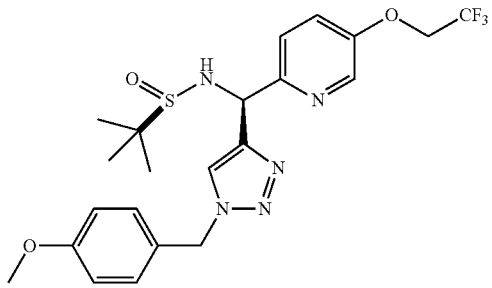 [SMILES: COc1ccc(Cn2cc([C@@H](N[S@](=O)C(C)(C)C)c3ccc(OCC(F)(F)F)cn3)nn2)cc1]

N-{(S)-[1-(4-methoxybenzyl)-1H-1,2,3-triazol-4-yl][5-(2,2,2-trifluoroethoxy)pyridin-2-yl]methyl}-2-(R)-methylpropane-2-sulfinamide To a solution of 2-(R)-methyl-N-{(1R)-1-[5-(2,2,2-trifluoroethoxy)pyridin-2-yl]prop-2-yn-1-yl}propane-2-sulfinamide (0.51 g, 1.5 mmol) in a mixture t-BuOH (50 mL) and water (5 mL) was added 1-(azidomethyl)-4-methoxybenzene (0.25 mL, 1.5 mmol) followed by sodium ascorbate (0.15 mL, 1 M) and CuSO$_4$ (0.015 mL, 1M). The reaction was stirred at room temperature for overnight. The reaction mixture was diluted with H$_2$O and the product precipitated as a dark oily residue. The solvents were removed by decant. The residue was dissolved in EtOAc, dried with Na$_2$SO$_4$, filtered and concentrated. The residue was purified by silica gel flash chromatography (50-100 EtOAc/hexanes) to give the product (0.46 g, 61%). ES-MS [M+1]$^+$: 498.1. $^1$H NMR (CDCl$_3$, 400 MHz) δ 8.26 (d, J=3.2 Hz, 1H), 7.46 (d, J=8.8 Hz, 1H), 7.33 (s, 1H), 7.23 (dd, J=2.8, 8.8 Hz, 1H), 7.20 (d, J=6.8 Hz, 2H), 6.88 (d, J=6.8 Hz, 2H), 5.82 (d, J=5.6 Hz, 1H), 5.42 (Abq, J=14.4, 20.0 Hz, 2H), 5.27 (d, J=5.6 Hz, 1H), 4.37 (q, J=8.06 Hz, 2H), 3.80 (s, 3H), 1.22 (s, 9H).

EXAMPLE 7

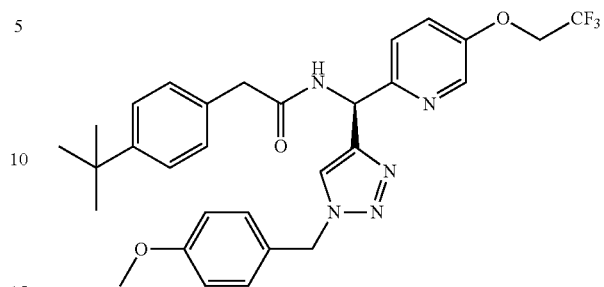

2-(4-tert-butylphenyl)-N-{(S)-[1-(4-methoxybenzyl)-1H-1,2,3-triazol-4-yl][5-(2,2,2-trifluoroethoxy)pyridin-2-yl]methyl}acetamide To a solution of N-{(S)-[1-(4-methoxybenzyl)-1H-1,2,3-triazol-4-yl][5-(2,2,2-trifluoroethoxy)pyridin-2-yl]methyl}-2-(R)-methylpropane-2-sulfinamide (0.46 g, 0.93 mmol) in MeOH (1.5 mL) was added a solution of HCl in ether (1.4 mL, 2 M). The reaction was stirred at room temperature for 1 h. The solvents were removed by concentration. The resulted amine bis-HCl salt (0.10 g, 0.22 mmol) was mixed with 4-t-butylpheylacetic acid (0.043 g, 0.22 mmol), HOAt (0.033 g, 0.25 mmol), EDC (0.047 g, 0.25 mmol) and diisopropylethyl amine (0.074 mL, 0.45 mmol) in CH$_2$Cl$_2$ (2.5 mL) and stirred at room temperature for 0.5 h. The solvent was removed and the residue was purified by reverse-phase HPLC to give the product (0.080 g, 63%). $^1$H NMR (CDCl$_3$, 400 MHz) δ 8.23 (d, J=2.4 Hz, 1H), 7.50 (d, J=6.8 Hz, 1H), 7.36-7.32 (m, 4H), 7.24 (dd, J=3.2, 8.8 Hz, 1H), 7.19 (d, J=8.4 Hz, 4H), 6.90-6.87 (d, J=8.8 Hz, 2H), 6.28 (d, J=6.8 Hz, 1H), 5.37 (s, 2H), 4.36 (q, J=8.0 Hz, 2H), 3.81 (s, 3H), 3.59 (s, 2H), 1.31 (s, 9H). HRMS (ES) [M+1]$^+$ calcd for C$_{30}$H$_{32}$F$_3$N$_5$O$_3$: 568.2530. Found: 568.2586.

EXAMPLE 8

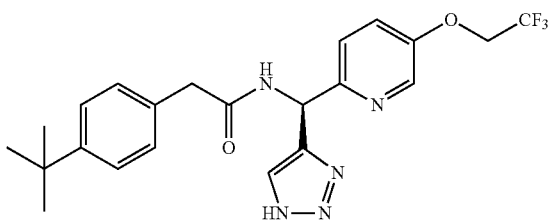 [SMILES: CC(C)(C)c1ccc(CC(=O)N[C@@H](c2ccc(OCC(F)(F)F)cn2)c2c[nH]nn2)cc1]

2-(4-tert-butylphenyl)-N-{(S)-1H-1,2,3-triazol-4-yl[5-(2,2,2-trifluoroethoxy)pyridin-2-yl]methyl}acetamide 2-(4-tert-butylphenyl)-N-{(S)-[1-(4-methoxybenzyl)-1H-1,2,3-triazol-4-yl][5-(2,2,2-trifluoroethoxy)pyridin-2-yl]methyl}acetamide (0.064 g, 0.11 mmol) was dissolved in TFA (1.0 mL) and heated at 65° C. for 6 h. The solvent was removed by N2 and the residue was purified by reverse-phase HPLC to give the product (0.046 g, 91%). $^1$H NMR (CDCl$_3$, 400 MHz) δ 8.30 (d, J=2.8 Hz, 1H), 7.94 (d, J=6.8 Hz, 1H), 7.49 (s, 1H), 7.45 (d, J=8.8 Hz, 1H), 7.39 (dd, J=2.8, 8.8 Hz, 1H), 7.34 (d, J=8.4 Hz, 2H), 7.20 (d, J=8.4 Hz, 2H), 6.39 (d, J=6.8 Hz, 1H), 4.41 (q, J=8.0 Hz, 2H), 3.63 (s, 2H), 1.30 (s, 9H). HRMS (ES) [M+1]$^+$ calcd for $C_{22}H_{24}F_3N_5O_2$: 448.1955. Found: 448.1976.

INTERMEDIATE 18

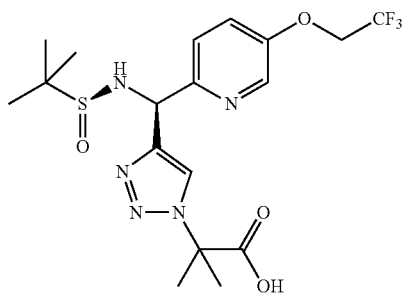 [SMILES: CC(C)(C(=O)O)n1cc([C@@H](N[S@@](=O)C(C)(C)C)c2ccc(OCC(F)(F)F)cn2)nn1]

2-(4-{(S)-[(tert-butylsulfinyl)amino][5-(2,2,2-trifluoroethoxy)pyridin-2-yl]methyl}-1H-1,2,3-triazol-1-yl)-2-methylpropanoic acid To a solution of 0.50 g (1.5 mmol) 2-methyl-N-{(1R)-1-[5-(2,2,2-trifluoroethoxy)pyridin-2-yl]prop-2-ynyl}propane-2-sulfinamide in 3.0 mL water and 3.0 mL t-butanol was added 1.8 mL (1.5 mmol) 2-azido-2-methyl-propanoic acid, 0.15 mL (0.15 mmol) 1.0M aqueous sodium ascorbate solution, and 15 µL (0.02 mmol) 1.0M solution of aqueous copper (II) sulfate. After 24 h at room temperature, the reaction mixture was quenched with water, acidified with 1N HCl, extracted three times with ethyl acetate, and washed with brine. The organic layer was dried over NaSO$_4$, filtered and concentrated in vacuo. Purification by flash chromatography (silica gel, linear gradient 0-20% MeOH:CH$_2$Cl$_2$) afforded 0.30 g (44%) 2-(4-{(S)-[(tert-butylsulfinyl)amino][5-(2,2,2-trifluoroethoxy)pyridin-2-yl]methyl}-1H-1,2,3-triazol-1-yl)-2-methylpropanoic acid. ES-MS [M+1]$^+$=464.2.

INTERMEDIATE 19

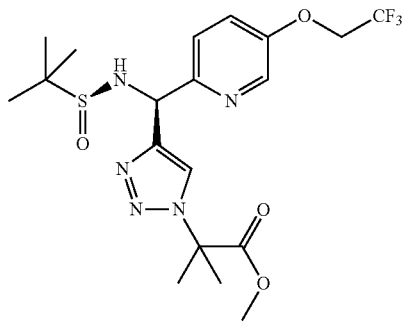 [SMILES: COC(=O)C(C)(C)n1cc([C@@H](N[S@@](=O)C(C)(C)C)c2ccc(OCC(F)(F)F)cn2)nn1]

Methyl 2-(4-{(S)-[(tert-butylsulfinyl)amin][5-(2,2,2-trifluoroethoxy)pyridin-2-yl]methyl}-1H-1,2,3-triazol-1-yl)-2-methylpropanoate To a solution of 0.30 g (0.65 mmol) 2-(4-{(S)-[(tert-butyl-sulfinyl)amino][5-(2,2,2-trifluoroethoxy)pyridin-2-yl]me-thyl}-1H-1,2,3-triazol-1-yl)-2-methylpropanoic acid in 2.5 ml toluene and 0.81 ml MeOH at rt was added 1.3 ml (2.6 mmol) 2.0 M TMS-diazomethane in hexanes. After 4 h at room temperature, the reaction mixture was concentrated in vacuo. Purification by flash chromatography (silica gel, linear gradient 0-15% MeOH in CH$_2$Cl$_2$) afforded 0.12 g (38%) methyl 2-(4-{(S)-[(tert-butylsulfinyl)amino][5-(2,2,2-trifluoroethoxy)pyridin-2-yl]methyl}-1H-1,2,3-triazol-1-yl)-2-methylpropanoate. ES-MS [M+1]$^+$=478.2. $^1$H NMR (CDCl$_3$, 400 MHz) δ 8.29 (d, J=2.75 Hz, 1H), 7.59 (s, 1H), 7.48 (d, J=8.70 Hz, 1H), 7.24 (m, 1H); 5.87 (d, J=5.31 Hz, 1H,), 5.33 (d, J=5.31 Hz, 1H), 4.38 (q, J=7.70 Hz, 2H), 3.71 (d, J=0.82 Hz, 1H); 1.92 (d, J=1.65 Hz, 6H); 1.27 (s, 9H).

INTERMEDIATE 20

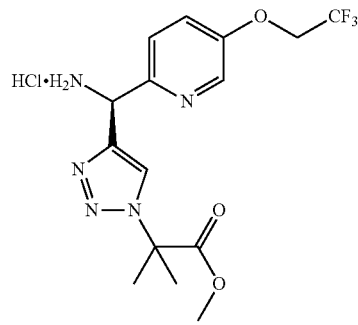

(S)-[1-(2-methoxy-1,1-dimethyl-2-oxoethyl)-1H-1,2,3-triazol-4-yl][4-(2,2,2-trifluoroethoxy)phenyl]methanaminium chloride To a solution of 0.12 g (0.25 mmol) methyl 2-(4-{(S)-[(tert-butylsulfinyl)amino][5-(2,2,2-trifluoroethoxy)pyridin-2-yl]methyl}-1H-1,2,3-triazol-1-yl)-2-methylpropanoate in 1.0 ml MeOH was added 0.96 mL (1.9 mmol) 2.0M HCl in diethyl ether. After 30 min at room temperature, the reaction mixture was concentrated in vacuo to afford (S)-[1-(2-methoxy-1,1-dimethyl-2-oxoethyl)-1H-1,2,3-triazol-4-yl][4-(2,2,2-trifluoroethoxy)phenyl]methanaminium chloride. ES-MS [M+1]$^+$=374.1.

EXAMPLE 9

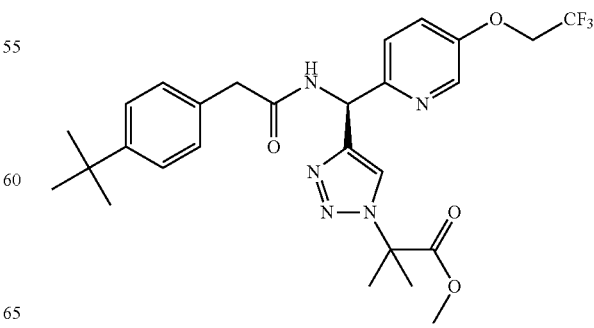

Methyl 2-(4-{(S)-{[(4-tert-butylphenyl)acetyl]amino}[5-(2,2,2-trifluoroethoxy)pyridin-2-yl]methyl}-1H-1,2,3-triazol-1-yl)-2-methylpropanoate To a solution of 0.05 g (0.26 mmol) (4-tert-butylphenyl)acetic acid in 0.50 ml CH$_2$Cl$_2$ was added 0.12 g (0.26 mmol) (S)-[1-(2-methoxy-1,1-dimethyl-2-oxoethyl)-1H-1,2,3-triazol-4-yl][4-(2,2,2-trifluoroethoxy)phenyl]methanaminium chloride, 0.05 g (0.34 mmol) HOAT, 0.07 g (0.34 mmol) EDC, and 0.14 ml (0.78 mmol) triethylamine. After 1 h at room temperature, the reaction mixture was diluted with CH$_2$Cl$_2$, and washed twice with water. The organic layer was dried over sodium sulfate, filtered and concentrated in vacuo. Purification by preparative HPLC (5->95% CH$_3$CN/H$_2$O over 15 min, 0.05% added TFA, C18) afforded 0.06 g (42%) methyl 2-(4-{(S)-{[(4-tert-butylphenyl)acetyl]amino}[5-(2,2,2-trifluoroethoxy)pyridin-2-yl]methyl}-1H-1,2,3-triazol-1-yl)-2-methylpropanoate. ES-MS [M+1]$^+$=548.3.

EXAMPLE 10

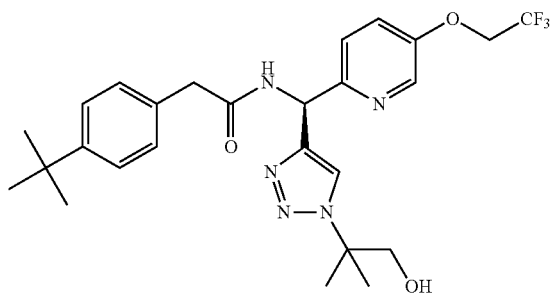 [SMILES: CC(C)(C)c1ccc(CC(=O)N[C@@H](c2ccc(OCC(F)(F)F)cn2)c2cn(C(C)(C)CO)nn2)cc1]

2-(4-tert-butylphenyl)-N-{(S)-[1-(2-hydroxy-1,1-dimethylethyl)-1H-1,2,3-triazol-4-yl][5-(2,2,2-trifluoroethoxy)pyridin-2-yl]methyl}acetamide To a solution of 0.06 g (0.11 mmol) methyl 2-(4-{(S)-{[(4-tert-butylphenyl)-acetyl]amino}[5-(2,2,2-trifluoroethoxy)pyridin-2-yl]methyl}-1H-1,2,3-triazol-1-yl)-2-methylpropanoate in 0.50 ml THF at rt was added 0.13 ml (0.26 mmol) 2.0 M lithium borohydride in THF. After 2 h at room temperature, the reaction-mixture was quenched with a few drops of water and concentrated in vacuo. Purification by preparative HPLC (5->95% CH$_3$CN/H$_2$O over 15 min, 0.05% added TFA, C18) afforded 0.02 g (40%) 2-(4-tert-butylphenyl)-N-{(S)-[1-(2-hydroxy-1,1-dimethylethyl)-1H-1,2,3-triazol-4-yl][5-(2,2,2-trifluoroethoxy)pyridin-2-yl]methyl}acetamide. ES-MS [M+1]$^+$=520.2. $^1$H NMR (CDCl$_3$, 400 MHz) δ 8.27 (d, 1H, J=2.83 Hz), 7.78 (br d, 1H, J=6.78 Hz), 7.57 (s, 1H), 7.49 (d, 1H, J=8.60 Hz), 7.39-7.36 (dd, 1H, J=2.93 Hz, 19.7 Hz), 7.36-7.23 (dd, 4H, J=8.24 Hz, 51.4 Hz), 6.36 (d, 1H, J=7.24 Hz), 4.41 (q, 2H, J=7.87 Hz), 3.83 (s, 2H), 3.62 (s, 2H), 1.56 (d, 6H, J=2.29 Hz), 1.31 (s, 9H).

EXAMPLE 11

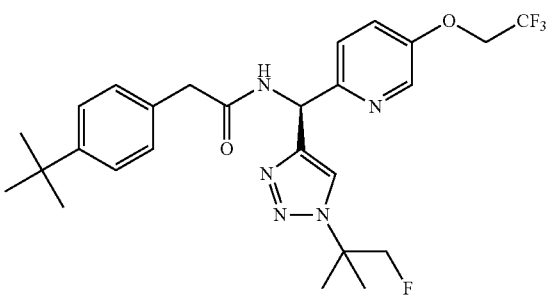 [SMILES: CC(C)(C)c1ccc(CC(=O)N[C@@H](c2ccc(OCC(F)(F)F)cn2)c2cn(C(C)(C)CF)nn2)cc1]

2-(4-tert-butylphenyl)-N-{(S)-[1-(2-fluoro-1,1-dimethylethyl)-1H-1,2,3-triazol-4-yl][5-(2,2,2-trifluoroethoxy)pyridin-2-yl]methyl}acetamide To a solution of 0.02 g (0.04 mmol) 2-(4-tert-butylphenyl)-N-{(S)-[1-(2-hydroxy-1,1-dimethylethyl)-1H-1,2,3-triazol-4-yl][5-(2,2,2-trifluoroethoxy)pyridin-2-yl]methyl}acetamide in 0.20 ml CH$_3$CN at rt was added 0.02 ml (0.13 mmol) DIEA, 0.009 ml (0.05 mmol) N,N-diisopropylethylamine trihydrofluoride, and 0.007 ml (0.04 mmol) perfluoro-1-butanesulfonyl fluoride (PBSF). After 2 h at room temperature, 0.007 ml (0.04 mmol) PBSF was added to the reaction mixture and the reaction was heated to 45° C. After 18 h at 45° C., the reaction temperature was increased to 60° C. After 4 h at 60° C., add 0.009 ml (0.05 mmol) N,N,-diisopropylethylamine trihydrofluoride and 0.007 ml (0.04 mmol) PBSF and continue heating. After 24 h, the reaction is still incomplete. At this point, the reaction mixture was quenched with water, filtered through a plug of silica and concentrated in vacuo. Purification by preparative HPLC (5->95% CH$_3$CN/H$_2$O over 15 min, 0.05% added TFA, C18) afforded 0.003 g (16%) 2-(4-tert-butylphenyl)-N-{(S)-[1-(2-fluoro-1,1-dimethylethyl)-1H-1,2,3-triazol-4-yl][5-(2,2,2-trifluoroethoxy)pyridin-2-yl]methyl}acetamide. ES-MS [M+1]$^+$=522.3. $^1$H NMR (CDCl$_3$, 400 MHz) 8.24 (d, 1H, J=2.65 Hz); 7.57 (s, 1H); 7.40-7.30 (m, 3H); 7.31-7.22 (m, 3H); 4.57-4.46 (d, 1H, J=47.2 Hz); 4.41 (q, 2H, J=8.06 Hz); 3.63 (s, 2H); 1.63 (s, 6H); 1.32 (s, 9H).

INTERMEDIATE 21

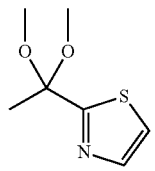

2-(1,1-dimethoxyethyl)-1,3-thiazole

A mixture of 1-(1,3-thiazol-2-yl)ethanone (35 g, 0.28 mol), anhydrous p-TsOH (50 g, 0.29 mol) and trimethyl orthoeformate (175 ml) in methanol (500 ml) was refluxed for 18 h. After concentration, the residue was partitioned between sat. NaHCO$_3$ and ether. The organic layers were washed with brine, dried over Na$_2$SO$_4$ and concentrated to give 36 g (75.6%) of 2-(1,1-dimethoxyethyl)-1,3-thiazole as an oil.

INTERMEDIATE 22

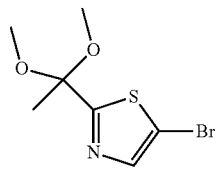

5-bromo-2-(1,1-dimethoxyethyl)-1,3-thiazole

To a solution of 2-(1,1-dimethoxyethyl)-1,3-thiazole (40 g, 0.23 mol) in THF (600 ml) was added n-BuLi (100 ml, 0.25 mol) dropwise at −78° C. After stirring for 1 h at −78° C., a solution of CBr$_4$ (300 g, 0.9 mol) in THF (300 ml) was added drop-wise. The reaction mixture was stirred for another 1 h at −78° C., and then was quenched by the addition of sat. aq. NH$_4$Cl and was extracted with ethyl acetate (150 ml×3). The organic layers were washed with brine, dried over Na$_2$SO$_4$ and concentrated. The residue was purified by column (eluted by petroleum ether/EtOAc=10:1) to afforded 25 g of 5-bromo-2-(1,1-dimethoxyethyl)-1,3-thiazole as solid (43%). $^1$H-NMR (CDCl$_3$ 400 MHz) δ 7.81 (s, 1H, Ar—H), 3.23 (s, 6H, —OCH$_3$), 1.72 (s, 3H, —CH$_3$).

INTERMEDIATE 23

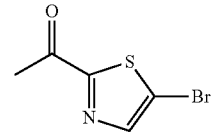

1-(5-bromo-1,3-thiazol-2-yl)ethanone

A solution of 5-bromo-2-(1,1-dimethoxyethyl)-1,3-thiazole (35 g) was dissolved in acetone (200 ml) and water (200 ml), was added con. HCl (40 ml). The mixture was stirred for 5 h at room temperature. After concentration to remove acetone, the residue was adjusted to pH=7 by the addition of NaHCO$_3$ and extracted with ether (30 ml×3). The organic layers were washed with brine, dried over Na$_2$SO$_4$ and concentrated to afford 25 g of 1-(5-bromo-1,3-thiazol-2-yl)ethanone as solid (87.4%). $^1$H-NMR (CDCl$_3$ 400 MHz) δ 7.87 (s, 1H, Ar—H), 2.66 (s, 3H, —CH$_3$)

INTERMEDIATE 24

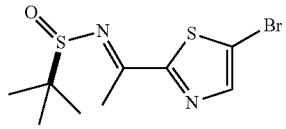

N-[1-(5-bromo-1,3-thiazol-2-yl)ethylidene]-2-methylpropane-2-sulfinamide

To a solution of 1-(5-bromo-1,3-thiazol-2-yl)ethanone (2.8 g, 13.6 mmol) in THF (60 ml), was added into R-Ellmann reagent (1.65 g, 13.6 mmol) and Ti(OEt)$_4$ (6.2 g, 27.2 mmol). After being refluxed for 16 h and cooling, to the mixture was added brine, and the mixture was stirred for another 30 min. The solid was removed by filtration, and the organic layer was dried over Na$_2$SO$_4$ and purified by column (eluted by PE:EA=5:1) to give 2.6 g of N-[-1-(5-bromo-1,3-thiazol-2-yl)ethylidene]-2-methylpropane-2-sulfinamide as yellow solid (61.9%). $^1$H-NMR (400 MHz CDCl$_3$) δ 7.81 (s, 1H, Ar—H), 2.80 (s, 3H, —CH$_3$), 1.32 (s, 9H, —C(CH$_3$)$_3$)

INTERMEDIATE 25

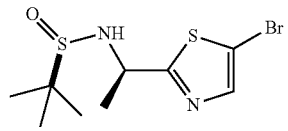

N-[(1R)-1-(5-bromo-1,3-thiazol-2-yl)ethyl]-2-methylpropane-2-sulfinamide

Dibal-H (20 ml, 20 mmol) was added into a solution of N-[-1-(5-bromo-1,3-thiazol-2-yl)ethylidene]-2-methylpropane-2-sulfinamide (2.2 g, 7.1 mmol) in THF (100 ml) at 78° C. After stirring an hour at −78° C., to the mixture was added ethanol (2 ml), and the mixture was quenched with sat. aq. potassium sodium tartrate. The aqueous layer was extracted with ethyl acetate (10 ml×3). The combined organic layers were dried over Na$_2$SO$_4$, and purified by silica to give 1.6 g of N-[(1R)-1-(5-bromo-1,3-thiazol-2-yl)ethyl]-2-(R)-methylpropane-2-sulfinamide as an oil (72%). $^1$H-NMR (CDCl$_3$ 400 MHz) δ 7.60 (s, 1H, Ar—H), 4.78 (m, 1H, —CHCH$_3$), 4.16 (d, J=4.4 Hz, —NH), 1.64 (d, J=6.4 Hz, 3H, —CH$_3$), 1.25 (s, 9H, —C(CH$_3$)$_3$)

INTERMEDIATE 26

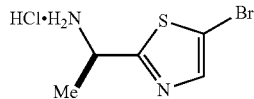

(1R)-1-(5-bromo-1,3-thiazol-2-yl)ethanamine hydrochloride

A solution of N-[(1R)-1-(5-bromo-1,3-thiazol-2-yl)ethyl]-2-(R)-methylpropane-2-sulfinamide (13 g, 4.1 mmol) in HCl-MeOH (300 ml) was stirred overnight at room temperature. After concentration to remove methanol, fresh ethanol was added, and the mixture was concentrated again. The crude solid was recrystallized to afford 8.5 g of (1R)-1-(5-bromo-1,3-thiazol-2-yl)ethanamine hydrochloride as colorless solid (87.3%). $^1$H-NMR (DMSO-d$_6$ 300 MHz) δ 8.78 (br, 3H, —NH$_3^+$), 7.96 (s, 1H), 4.80 (q, J=6.9 Hz, 1H, —CHCH$_3$), 1.57 (d, J=6.9 Hz, —CH$_3$)

INTERMEDIATE 27

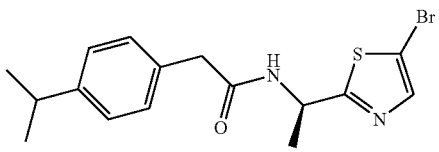 [SMILES: CC(C)c1ccc(CC(=O)N[C@H](C)c2ncc(Br)s2)cc1]

N-[(1R)-1-(5-bromo-1,3-thiazol-2-yl)ethyl]-2-[4-(propan-2-yl)phenyl]acetamide

To a solution of 0.050 g (0.28 mmol) 4-isopropylphenyl acetic acid in 0.50 mL DMF and 1.0 mL CH$_2$Cl$_2$ was added 0.072 g (0.30 mmol) (1R)-1-(5-bromo-1,3-thiazol-2-yl)ethanamine hydrochloride, 0.042 g (0.31 mmol) HOAT, 0.059 g (0.31 mmol) EDC, and 0.093 mL (0.56 mmol) DIEA. After 1 h at room temperature, the reaction mixture was purified by preparative reverse-phase HPLC (5->95% CH$_3$CN/H$_2$O over 15 min, 0.05% added TFA, C18) to give N-[(1R)-1-(5-bromo-1,3-thiazol-2-yl)ethyl]-2-[4-(propan-2-yl)phenyl]acetamide. $^1$H NMR (CDCl$_3$, 400 MHz) δ 7.54 (s, 1H); 7.59 (ABq, J=8.4 Hz, 4H), 6.55 (br d, J=7.6 Hz, 1H), 5.32 (quintet, J=7.2 Hz, 1H), 3.59 (s, 2H), 2.91 (m, J=7.2 Hz, 3H); 1.52 (d, J=7.2 Hz, 3H), 1.25 (d, J=7.2 Hz, 6H). HRMS (ES) [M+1]$^+$ calcd for C$_{16}$H$_{19}$BrN$_2$OS: 367.0474. Found: 367.0483.

INTERMEDIATE 28

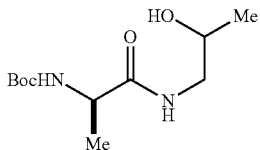 [SMILES: CC(O)CNC(=O)[C@@H](C)NC(=O)OC(C)(C)C]

N$^2$-(tert-butoxycarbonyl)-N-(2-hydroxypropyl)-D-alaninamide

A mixture of CDI (19 g, 0.12 mol), Boc-D-alanine (20 g, 0.11 mol) and DCM (300 ml), was stirred at r.t. for 1 h, before 1-amino-2-propanol (14 ml, 0.18 mol) was added. The reaction mixture was stirred at r.t. overnight. After concentration, the residue was purified by column, and 13 g (46.3%) of N$^2$-(tert-butoxycarbonyl)-N-(2-hydroxypropyl)-D-alaninamide as solid was obtained. ES-MS [M+1]$^+$: 247.01.

INTERMEDIATE 29

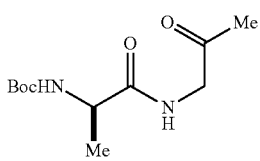 [SMILES: CC(=O)CNC(=O)[C@@H](C)NC(=O)OC(C)(C)C]

N$^2$-(tert-butoxycarbonyl)-N-(2-oxopropyl)-D-alaninamide

To a solution of N$^2$-(tert-butoxycarbonyl)-N-(2-hydroxypropyl)-D-alaninamide (13 g, 53 mmol) in acetonitrile (800 ml) and water (320 ml), was added RuCl$_3$ (300 mg, 1.06 mmol) and NaBrO$_3$ (4 g, 26.5 mmol). The resulting mixture was stirred at room temperature overnight. After concentration to remove most of acetonitrile, the residue was departed between water and ethyl acetate. The organic layer was washed with water, brine, dried over Na$_2$SO$_4$, filtered and concentrated to give 8.5 g (65.9%) of N$^2$-(tert-butoxycarbonyl)-N-(2-oxopropyl)-D-alaninamide as solid. $^1$H-NMR CDCl$_3$ δ 6.86 (br, 1H), 5.08 (br, 1H), 4.13 (s, 2H), 5.09 (s, 2H), 2.19 (s, 3H), 1.43 (s, 9H), 1.37 (s, 3H). ES-MS [M+1]$^+$: 244.90

INTERMEDIATE 30

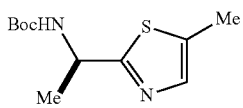 [SMILES: Cc1cnc([C@@H](C)NC(=O)OC(C)(C)C)s1]

tert-butyl [(1R)-1-(5-methyl-1,3-thiazol-2-yl)ethyl]carbamate

Lawesson's Reagent (14 g, 35 mmol) was added to a solution of N$^2$-(tert-butoxycarbonyl)-N-(2-oxopropyl)-D-alaninamide (8.5 g, 34.5 mmol) in THF (300 ml), and the resulting mixture was refluxed for 6 h. After concentration, the residue was purified by column, and 2.8 g of tert-butyl [(1R)-1-(5-methyl-1,3-thiazol-2-yl)ethyl]carbamate was obtained as solid (35%). $^1$H-NMR CDCl$_3$ δ 7.31 (s, 1H), 5.24 (br, 1H), 5.00 (m, 1H), 2.42 (s, 3H), 1.55 (d, J=6.8 Hz, 3H), 1.44 (s, 9H) ES-MS [M+1]$^+$: 243.14.

INTERMEDIATE 31

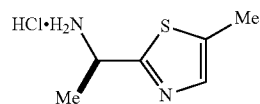

(1R)-1-(5-methyl-1,3-thiazol-2-yl)ethanamine hydrochloride tert-butyl [(1R)-1-(5-methyl-1,3-thiazol-2-yl)ethyl]carbamate (2.8 g, 11.5 mmol) was dissolved into HCl-MeOH (40 ml), and the resulting mixture was stirred at r.t. for 2 h. After concentration to remove most of solvent, to the residue was added fresh ethanol, and the residue was concentrated again.

The crude product was recrystallized from ethanol and ether to give 1.8 g (87.8%) of (1R)-1-(5-methyl-1,3-thiazol-2-yl)ethanamine hydrochloride as solid hydrochloric salt. $^1$H-NMR DMSO δ 8.76 (br, 3H), 7.52 (s, 1H), 4.69 (m, 1H), 1.56 (d, J=6.8 Hz, 3H). ES-MS [M+1]$^+$: 143.25.

EXAMPLE 12

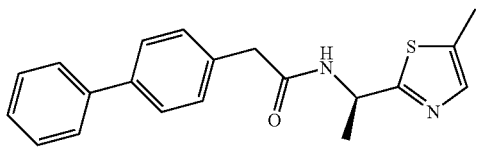 [SMILES: Cc1cnc([C@@H](C)NC(=O)Cc2ccc(-c3ccccc3)cc2)s1]

2-(biphenyl-4-yl)-N-[(1R)-1-(5-methyl-1,3-thiazol-2-yl)ethyl]acetamide

To a solution of 0.05 g (0.24 mmol) 1,1'-biphenyl-4-ylacetic acid in 0.50 ml DMF was added 0.05 g (0.24 mmol) 2-[(1R)-1-ammonioethyl]-5-methyl-1,3-thiazol-3-ium dichloride, 0.04 g (0.31 mmol) HOAT, 0.60 g (0.31 mmol) EDC, and 0.12 mL (0.71 mmol) DIEA. After 24 h at room temperature, the reaction mixture was purified by preparative HPLC (5->95% CH$_3$CN/H$_2$O over 15 min, 0.05% added TFA, C18) to afford 0.70 g (86%) 2-(biphenyl-4-yl)-N-[(1R)-1-(5-methyl-1,3-thiazol-2-yl)ethyl]acetamide. $^1$H NMR (CDCl$_3$, 400 MHz) 7.59 (m, 4H), 7.44 (m, 2H), 7.35 (m, 4H), 6.55 (br d, 1H, J=7.32 Hz), 5.43 (m, 1H), 3.65 (s, 2H), 2.43 (s, 3H), 1.55 (d, 3H, J=6.96 Hz). HRMS (ES) [M+1]$^+$ calcd for C$_{20}$H$_{21}$N$_2$OS: 337.1375. Found: 337.1368.

INTERMEDIATE 32

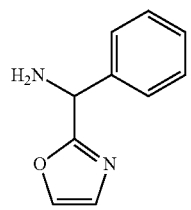

1-(1,3-oxazol-2-yl)-1-phenylmethanamine 1,3-Oxazol-2-yl(phenyl)methanol (0.21 g, 1.2 mmol) was dissolved in SOCl$_2$ (7.0 mL) and stirred at room temperature for 4 h. The mixture was concentrated to remove excess SOCl$_2$. The residue SOCl$_2$ was removed by co-evaporation with CH2Cl2 for three times. The crude chloride was dissolved in THF (2 mL) and 2 mL of NH$_4$OH was added. The mixture was stirred at room temperature overnight, and conc. The crude product, 1-(1,3-oxazol-2-yl)-1-phenylmethanamine was dried and used for next reaction without purification.

EXAMPLE 13

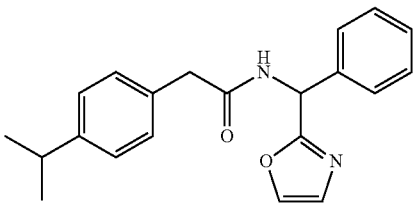 [SMILES: CC(C)c1ccc(CC(=O)NC(c2ccccc2)c2ncco2)cc1]

N-[1,3-oxazol-2-yl(phenyl)methyl]-2-[4-(propan-2-yl)phenyl]acetamide

The crude 1-(1,3-oxazol-2-yl)-1-phenylmethanamine (0.10 g, 0.57 mmol) was mixed with 4-isopropylpheylacetic acid (0.10 g, 0.57 mmol), HOAt (0.086 g, 0.63 mmol) and EDC (0.12 g, 0.63 mmol) in DMF (1.0 mL) and stirred at room temperature for 0.5 h. Purification by reverse-phase HPLC gave the product (0.025 g, 13%). ES-MS [M+1]$^+$: 335.1. $^1$H NMR (CDCl$_3$, 400 MHz) δ 7.58 (s, 1H), 7.31-7.28 (m, 3H), 7.22-7.20 (m, 6H), 7.07 (s, 1H), 6.73 (d, J=8.0 Hz, 1H), 6.32 (d, J=7.6 Hz, 1H), 3.62 (s, 2H), 2.90 (m, J=6.8 Hz, 1H), 1.24 (d, J=6.8 Hz, 6H).

INTERMEDIATE 33

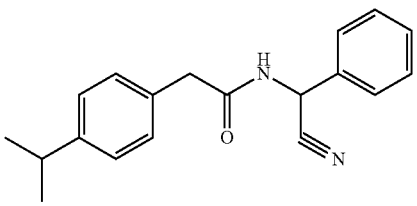 [SMILES: CC(C)c1ccc(CC(=O)NC(C#N)c2ccccc2)cc1]

N-[cyano(phenyl)methyl]-2-(4-isopropylphenyl)acetamide

To a 100 ml round bottom flask equipped with a magnetic stir bar were added 4-isopropylphenylacetic acid (1.786 g, 10.02 mmol), cyano(phenyl)-methanaminium chloride (1.690 g, 10.02 mmol), 1-(3-dimethylaminopropyl)-3-ethyl-carbodiimide hydrochloride (1.921 g, 10.02 mmol), 1-hydroxy-7-azabenzotriazole (1.364 g, 10.02 mmol) and triethylamine (3.042 ml, 30.06 mmol) into 30.0 ml of CH$_2$Cl$_2$. The resulting solution was stirred at room temperature for 16 hours. The reaction mixture was diluted with water and the two layers were separated. The aqueous layer was extracted with CH$_2$Cl$_2$. The combined organic layers were washed with brine, dried over anhydrous Na$_2$SO$_4$ and filtered. The filtrate was concentrated in vacuum. Purification by preparative HPLC (20-90% CH$_3$CN/H$_2$O over 30 min, 0.05% added TFA, C18 column) to afford 1.6 g (54%) of the title compound. $^1$H NMR (CDCl$_3$, 400 MHz) δ 7.382 (m, 5H), 7.206 (m, 4H), 6.156 (d, J=8.6 Hz, 1H), 5.997 (br d, J=8.2 Hz, 1H), 3.632 (s, 2H), 2.895 (sept, J=7.0 Hz, 1H), 1.238 (d, J=7.0 Hz, 6H). ES-MS [M+1]$^+$: 293.2.

EXAMPLE 14

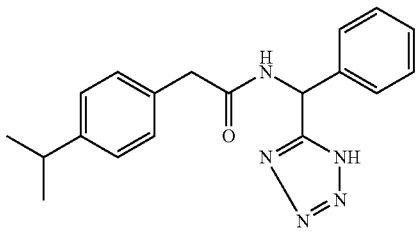 [SMILES: CC(C)c1ccc(CC(=O)NC(c2ccccc2)c2nnn[nH]2)cc1]

2-(4-isopropylphenyl)-N-[phenyl(1H-tetrazol-5-yl)methyl]acetamide

To a solution N-[cyano(phenyl)methyl]-2-(4-isopropylphenyl)acetamide (58.0 mg, 0.198 mmol) in 0.5 ml of anhydrous DMF was added NH$_4$Cl (12.0 mg, 0.218 mmol) and NaN$_3$ (14.00 mg, 0.218 mmol). The resulting solution was stirred at 110° C. for 16 hour. Filtered and the filtrate was purified by preparative HPLC (5-90% CH$_3$CN/H$_2$O over 30 min, 0.05% added TFA, C18 column) to afford 53.0 mg (80%) of the title compound. $^1$H NMR (CD$_3$OD, 400 MHz) δ 7.326 (m, 5H), 7.169 (ABq, J=8.2 Hz, 4H), 6.460 (s, 1H), 3.583 (ABq, J=14.5 Hz, 2H), 2.856 (sept, J=7.0 Hz, 1H), 1.214 (d, J=7.0 Hz, 6H). ES-MS [M+1]$^+$: 336.2.

EXAMPLE 15

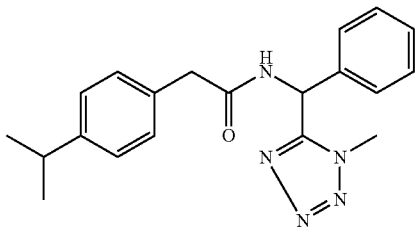 [SMILES: CC(C)c1ccc(CC(=O)NC(c2ccccc2)c2nnnn2C)cc1]

2-(4-isopropylphenyl)-N-[(1-methyl-1H-tetrazol-5-yl)(phenyl)methyl]acetamide

To a solution 2-(4-isopropylphenyl)-N-[phenyl(1H-tetrazol-5-yl)methyl]acetamide (34.0 mg, 0.101 mmol) in 0.5 ml of anhydrous DMF was added K$_2$CO$_3$ (14.0 mg, 0.101 mmol) and MeI (0.006 ml, 0.101 mmol). The resulting solution was stirred at RT for 3 hour. Filtered and the residue was purified by preparative HPLC (5-90% CH$_3$CN/H$_2$O over 30 min, 0.05% added TFA, C18 column) to afford 8.0 mg (23%) of the title compound. $^1$H NMR (CDCl$_3$, 400 MHz) δ 7.342 (m, 3H); 7.226 (m, 2H), 7.172 (ABq, J=8.2 Hz, 4H), 6.894 (br d, J=7.6 Hz, 1H), 6.424 (d, J=7.9 Hz, 1H), 3.910 (s, 3H), 3.587 (s, 2H), 2.888 (sept, J=7.0 Hz, 1H), 1.234 (d, J=7.0 Hz, 6H). ES-MS [M+1]$^+$: 350.2.

INTERMEDIATE 34

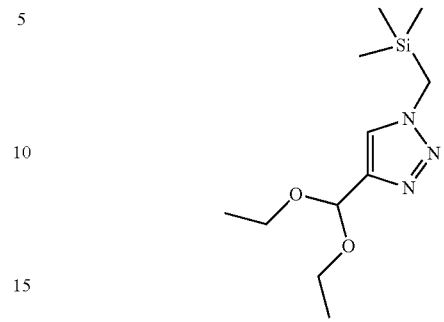

4-(Diethoxymethyl)-1-[(trimethylsilyl)methyl]-1H-1,2,3-triazole

To a 100 ml round bottom flask equipped with a magnetic stir bar were added (azidomethyl)(trimethyl)silane (1.000 g, 7.740 mmol), 3,3-diethoxyprop-1-yne (0.992 g, 7.740 mmol), freshly made 1.0N sodium asorbate (0.774 ml, 7.740 mmol), and 1.0N Cu$_2$SO$_4$ (0.774 ml, 7.740 mmol) into 30.0 ml of a mixed solvent BuOH/H$_2$O (1:1). The resulting solution was stirred at room temperature for 16 hours. The reaction mixture was diluted with water and extracted with EtOAc. The combined organic layers were washed with brine, dried over anhydrous Na$_2$SO$_4$ and filtered. The filtrate was concentrated in vacuum to give the crude title compound as a light yellow liquid (1.620 g, 81% crude). ES-MS [M+1]$^+$: 258.1 (M+H). This intermediate was carried over to the next step without further purifications and characterizations.

INTERMEDIATE 35

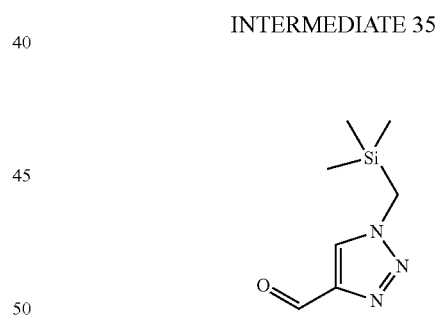

1-[(Trimethylsilyl)methyl]-1H-1,2,3-triazole-4-carbaldehyde

To a solution of 4-(diethoxymethyl)-1-[(trimethylsilyl)methyl]-1H-1,2,3-triazole (1.620 mg, 6.290 mmol) in 10.0 ml of THF was added 2.0N HCl in Et$_2$O (9.44 ml, 18.88 mmol), and the mixture was stirred at RT for 15 min. The reaction mixture was diluted with water and extracted with EtOAc. The combined organic layers were washed with brine, dried over anhydrous Na$_2$SO$_4$ and filtered. The filtrate was concentrated in vacuum to give the crude title compound as a light yellow liquid (1.050 g, 91% crude). ES-MS [M+1]$^+$: 184.1. This intermediate was carried over to the next step without further purifications and characterizations.

INTERMEDIATE 36

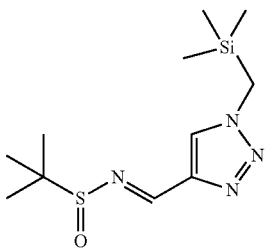 [SMILES: CC(C)(C)S(=O)/N=C/c1cn(C[Si](C)(C)C)nn1]

2-Methyl-N-((1E)-{1-[(trimethylsilyl)methyl]-1H-1,2,3-triazol-4-yl}methylene)propane-2-sulfinamide To a 50 ml round bottom flask equipped with a magnetic stir bar were added 1-[(Trimethylsilyl)methyl]-1H-1,2,3-triazole-4-carbaldehyde (1.042 g, 5.720 mmol), 4-tert-butylsulfinamide (0.693 g, 5.720 mmol), and $Cu_2SO_4$ (1.825 g, 11.44 mmol) into 15.0 ml of $CH_2Cl_2$. The resulting solution was stirred at room temperature for 16 hours. The combined organic layers were washed with brine, dried over anhydrous $Na_2SO_4$ and filtered. The filtrate was concentrated in vacuum to give the title compound as a clear liquid (1.080 g, 73%). $^1$H NMR ($CDCl_3$, 400 MHz) δ 8.760 (s, 1H), 7.902 (s, 1H), 3.971 (ABq, J=5.20 Hz, 2H), 1.252 (s, 9H), 0.177 (s, 9H). ES-MS $[M+1]^+$: 287.1.

INTERMEDIATE 37

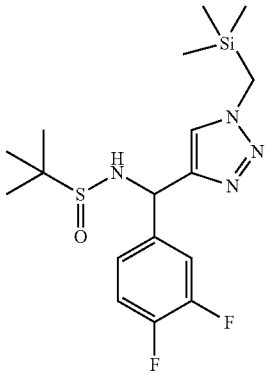 [SMILES: CC(C)(C)S(=O)NC(c1ccc(F)c(F)c1)c1cn(C[Si](C)(C)C)nn1]

N-((3,4-difluorophenyl){1-[(trimethylsilyl)methyl]-1H-1,2,3-triazol-4-yl}methyl)-2-methylpropane-2-sulfinamide To a 25 ml round bottom flask containing −78° C. solution of 2-methyl-N-((1E)-{1-[(trimethylsilyl)methyl]-1H-1,2,3-triazol-4-yl}methylene)propane-2-sulfinamide (0.286 g, 0.998 mmol) in 4.0 ml of $CH_2Cl_2$ was added dropwise 0.5N 3,4-difluorophenylmagnesium bromide in THF (4.990 ml, 1.495 mmol). The resulting solution was stirred at −78° C. for 30 min, then −20° C. for 16 hours. The reaction mixture was quenched with saturated $NH_4Cl$ and extracted with $CH_2Cl_2$. The combined organic layers were washed with brine, dried over anhydrous $Na_2SO_4$ and filtered. The filtrate was concentrated in vacuum to give the crude title compound as a light yellow liquid (0.498 g, 93% crude). ES-MS $[M+1]^+$: 401.1. This intermediate was carried over to the next step without further purifications and characterizations.

INTERMEDIATE 38

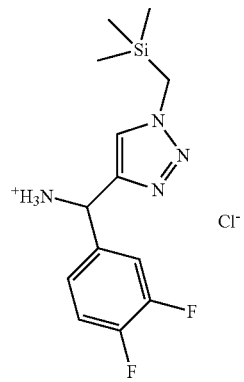 [SMILES: C[Si](C)(C)Cn1cc(C([NH3+])c2ccc(F)c(F)c2)nn1 ; [Cl-]]

(3,4-Difluorophenyl){1-[(trimethylsilyl)methyl]-1H-1,2,3-triazol-4-yl}methanaminium chloride To a solution of N-(3,4-difluorophenyl)-{1-[(trimethylsilyl)methyl]-1H-1,2,3-triazol-4-yl}methyl)-2-methylpropane-2-sulfinamide (0.498 mg, 1.243 mmol) in 5.0 ml of MeOH was added 2.0N HCl in $Et_2O$ (6.220 ml, 12.43 mmol), and the mixture was stirred at RT for 30 min. Solvent removed and the residue was dried under vacuum to give the crude title compound (0.500 g, 91%). ES-MS $[M+1]^+$: 297.1. This intermediate was carried over to the next step without further purification and characterization.

INTERMEDIATE 39

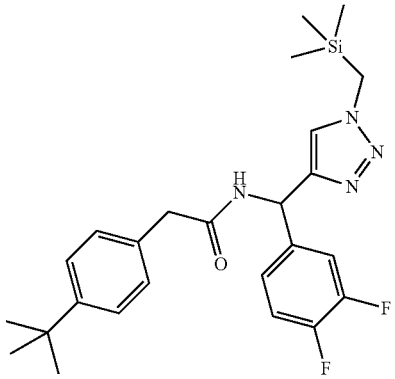 [SMILES: CC(C)(C)c1ccc(CC(=O)NC(c2ccc(F)c(F)c2)c2cn(C[Si](C)(C)C)nn2)cc1]

2-(4-tert-Butylphenyl)-N-((3,4-difluorophenyl){1-[(trimethylsilyl)methyl]-1H-1,2,3-triazol-4-yl}methyl)acetamide To a 50 ml round bottom flask equipped with a magnetic-stir bar were added (3,4-difluorophenyl){1-[(trimethylsilyl)

methyl]-1H-1,2,3-triazol-4-yl}methanaminium chloride (0.500 g, 1.502 mmol), 4-tert-butylphenylacetic acid (0.289 mg, 1.502 mmol), 1-(3-dimethylaminopropyl)-3-ethylcarbodiimide hydrochloride (0.288 g, 1.502 mmol), 1-hydroxy-7-azabenzotriazole (0.204 mg, 1.502 mmol) and triethylamine (0.629 ml, 2.253 mmol) into 10.0 ml of $CH_2Cl_2$. The resulting solution was stirred at room temperature for 2 hours. The reaction mixture was diluted with water and the two layers were separated. The aqueous layer was extracted with $CH_2Cl_2$. The combined organic layers were washed with brine, dried over anhydrous $Na_2SO_4$ and filtered. The filtrate was concentrated in vacuum. Purification by preparative HPLC (20-90% $CH_3CN/H_2O$ over 30 min, 0.05% added TFA, C18 column) to afford 0.536 g (67%) of the title compound. $^1H$ NMR ($CDCl_3$, 400 MHz) δ 7.347 (m, 2H), 7.190 (m, 3H), 7.040 (m, 2H), 6.970 (m, 2H), 6.223 (d, J=7.60 Hz, 1H), 3.852 (ABq, J=15.29 Hz, 2H), 3.580 (s, 2H), 1.305 (s, 9H), 0.125 (s, 9H). ES-MS $[M+1]^+$: 471.2.

EXAMPLE 16

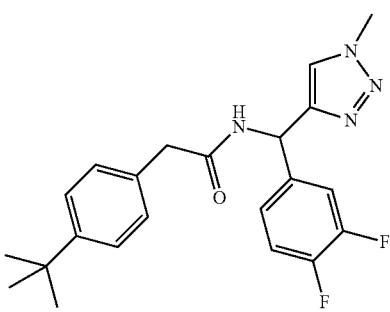 [SMILES: Cn1cc(C(NC(=O)Cc2ccc(C(C)(C)C)cc2)c2ccc(F)c(F)c2)nn1]

2-(4-tert-Butylphenyl)-N-[(3,4-difluorophenyl)(1-methyl-1H-1,2,3-triazol-4-yl)methyl]acetamide To a 10 ml round bottom flask containing a solution of 2-(4-tert-butylphenyl)-N-((3,4-difluorophenyl){1-[(trimethylsilyl)methyl]-1H-1,2,3-triazol-4-yl}-methyl)acetamide (0.062 mg, 0.132 mmol) in 1.0 ml of anhydrous THF at rt was added 1.0N tetrabutylammonium fluoride in THF (0.145 ml, 0.145 mmol). The resulting solution was stirred at room temperature for 1 hour. The reaction mixture was diluted with water and extracted with $CH_2Cl_2$. The combined organic layers were washed with brine, dried over anhydrous $Na_2SO_4$ and filtered. The filtrate was concentrated in vacuum. Purification by preparative HPLC (20-90% $CH_3CN/H_2O$ over 30 min, 0.05% added TFA, C18 column) to afford 0.046 g (88%) of the title compound. Purification by super fluid ($CO_2$/MeOH) chiral column yielded first enathiomer (19 mg) (36.2%), and second enathiomer (21 mg) (40%) $^1H$ NMR ($CDCl_3$, 400 MHz) δ 7.359 (m, 2H), 7.307 (s, 1H), 7.183 (m, 2H), 7.009 (m, 3H), 6.769 (d, J=7.32 Hz, 1H), 6.216 (d, J=7.57 Hz, 1H), 4.059 (s, 3H), 3.581 (ABq, J=15.75 Hz, 2H), 1.311 (s, 9H). ES-MS $[M+1]^+$: 399.2.

INTERMEDIATE 40

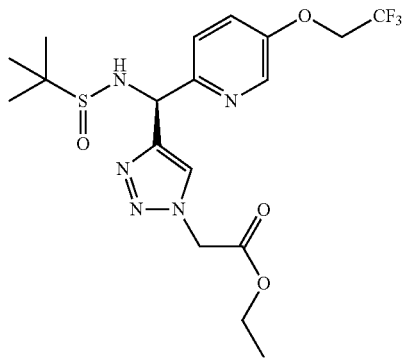 [SMILES: CCOC(=O)Cn1cc([C@@H](NS(=O)C(C)(C)C)c2ccc(OCC(F)(F)F)cn2)nn1]

Ethyl(4-{(S)-[(tert-butylsulfinyl)amino][5-(2,2,2-trifluoroethoxy)pyridin-2-yl]methyl}-1H-1,2,3-triazol-1-yl)acetate To a 50 ml round bottom flask equipped with a magnetic stir bar were added ethyl azidoacetate (0.193 g, 1.495 mmol), 2-methyl-N-{(1R)-1-[5-(2,2,2-trifluoroethoxy)pyridin-2-yl]prop-2-yn-1-yl}propane-2-sulfinamide (0.500 g, 1.495 mmol), freshly made 1.0 N sodium ascorbate (0.150 ml, 0.150 mmol), and 1.0 N $Cu_2SO_4$ (0.150 ml, 0.150 mmol) into 6.0 ml of a mixed solvent BuOH/$H_2O$ (1:1). The resulting solution was stirred at room temperature for 16 hours. The reaction mixture was diluted with water and extracted with EtOAc. The combined organic layers were washed with brine, dried over anhydrous $Na_2SO_4$ and filtered. The filtrate was concentrated in vacuum. Purification by flash chromatography ($SiO_2$, 50-80% ethyl acetate in hexanes, gradient) gave the title compound as a light yellow solid (0.365 g, 53%). $^1H$ NMR ($CDCl_3$, 400 MHz) δ 8.291 (d, J=2.93 Hz, 1H), 7.634 (s, 1H), 7.452 (d, J=8.79 Hz, 1H), 7.247 (ABq, J=3.03 Hz, 1H), 5.879 (d, J=5.50 Hz, 1H), 5.349 (d, J=5.31 Hz, 1H), 5.125 (ABq, J=7.49 Hz, 2H), 4.381 (q, J=7.87 Hz, 2H), 4.255 (q, J=7.14 Hz, 2H), 1.290 (t, J=7.14 Hz, 3H), 1.271 (s, 9H). ES-MS $[M+1]^+$: 464.1.

INTERMEDIATE 41

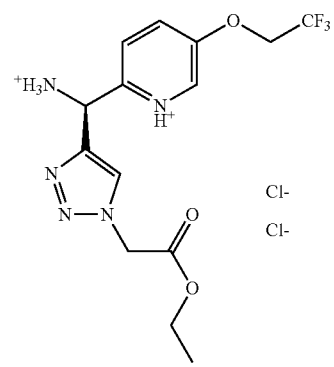

2-{(S)-ammonio[1-(2-ethoxy-2-oxoethyl)-1H-1,2,3-triazol-4-yl]methyl}-5-(2,2,2-trifluoroethoxy)pyridinium dichloride To a solution of ethyl(4-{(S)-[(tert-butylsulfinyl)amino][5-(2,2,2-trifluoroethoxy)pyridin-2-yl]methyl}-1H-1,2,3-triazol-1-yl)acetate (0.285 mg, 0.615 mmol) in 5.0 ml of EtOH was added 2.0N HCl in Et₂O (3.070 ml, 6.150 mmol), and the mixture was stirred at RT for 30 min. Solvent removed and the residue was dried under vacuum to give the crude title compound (0.260 g, 99%). ES-MS [M+1]⁺: 360.1. This intermediate was carried over to the next step without further purification and characterization.

INTERMEDIATE 42

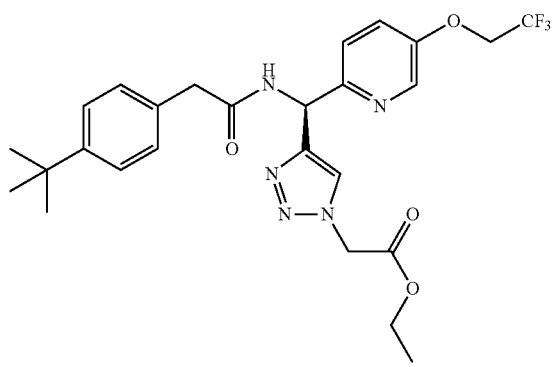 [SMILES: CCOC(=O)Cn1cc([C@@H](NC(=O)Cc2ccc(C(C)(C)C)cc2)c2ccc(OCC(F)(F)F)cn2)nn1]

Ethyl(4-{(S)-{[(4-tert-butylphenyl)acetyl]amino}[5-(2,2,2-trifluoroethoxy)pyridin-2-yl]methyl}-1H-1,2,3-triazol-1-yl)acetate To a 100 ml round bottom flask equipped with a magnetic stir bar were added 2-{(S)-ammonio[1-(2-ethoxy-2-oxoethyl)-1H-1,2,3-triazol-4-yl]methyl}-5-(2,2,2-trifluoroethoxy)pyridinium dichloride (0.265 g, 0.614 mmol), 4-tert-butylphenylacetic acid (0.118 g, 0.614 mmol), 1-(3-dimethylaminopropyl)-3-ethylcarbodiimide hydrochloride (0.118 g, 0.614 mmol), 1-hydroxy-7-azabenzotriazole (0.084 g, 0.614 mmol) and diisopropylethylamine (0.236 ml, 1.350 mmol) into 10.0 ml of CH₂Cl₂. The resulting solution was stirred at room temperature for 2 hours. The reaction mixture was diluted with water and the two layers were separated. The aqueous layer was extracted with CH₂Cl₂. The combined organic layers were washed with brine, dried over anhydrous Na₂SO₄ and filtered. The filtrate was concentrated in vacuum. Purification by preparative HPLC (20-90% CH₃CN/H₂O over 30 min, 0.05% added TFA, C18 column) to afford 0.150 g (46%) of the title compound. ¹H NMR (CDCl₃, 400 MHz) δ 8.219 (s, 1H), 7.610 (m, 2H), 7.340 (m, 3H), 7.255 (m, 1H), 7.184 (m, 2H), 6.322 (d, J=7.96 Hz, 1H), 5.041 (s, 2H), 4.347 (q, J=7.97 Hz, 2H), 4.210 (q, J=7.14 Hz, 2H), 3.912 (br s, 1H), 3.585 (s, 2H), 1.278 (s, 9H), 1.249 (t, J=7.19 Hz, 3H). ES-MS [M+1]⁺: 534.3.

EXAMPLE 17

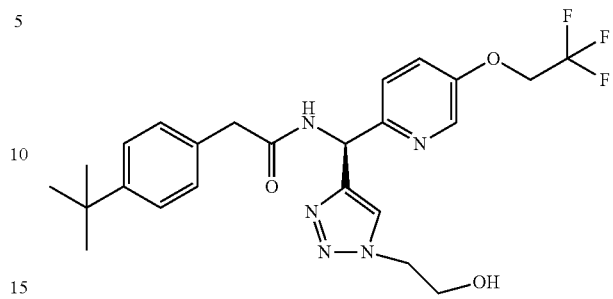

2-(4-tert-Butylphenyl)-N-{(S)-[1-(2-hydroxyethyl)-1H-1,2,3-triazol-4-yl][5-(2,2,2-trifluoroethoxy)pyridin-2-yl]methyl}acetamide To a solution of ethyl(4-{(S)-{[(4-tert-butylphenyl)acetyl]amino}[5-(2,2,2-trifluoroethoxy)pyridin-2-yl]methyl}-1H-1,2,3-triazol-1-yl)acetate (0.190 g, 0.356 mmol) in 1.0 ml of anhydrous THF at RT was added 2.0N LiBH₄ in THF (0.214 ml, 0.427 mmol). The resulting solution was stirred at room temperature for 16 hours. The reaction mixture was quenched with 1.0N HCl (2.0 ml, 2.000 mmol), stirred for 30 min. and 2.0 N NaOH (2.0 ml, 4.000 mmol) was added. The mixture was extracted with EtOAc. The combined organic layers were washed with brine, dried over anhydrous Na₂SO₄ and filtered. The filtrate was concentrated in vacuum. Purification by preparative HPLC (20-90% CH₃CN/H₂O over 30 min, 0.05% added TFA, C18 column) to afford 0.047 g (27%) of the title compound. ES-MS [M+1]⁺: 492.3. This intermediate was carried over to the next step without further purification and characterization.

EXAMPLE 18

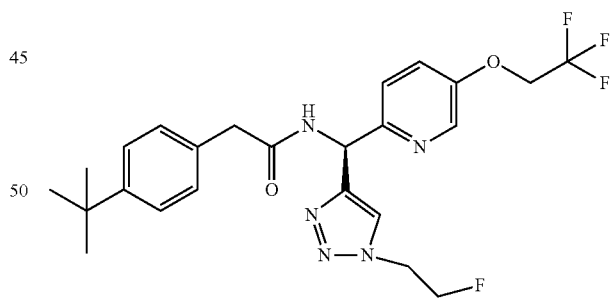

2-(4-tert-Butylphenyl)-N-{(S)-[1-(2-fluoroethyl)-1H-1,2,3-triazol-4-yl][5-(2,2,2-trifluoroethoxy)pyridin-2-yl]methyl}acetamide To a solution of 2-(4-tert-Butylphenyl)-N-{(S)-[1-(2-hydroxyethyl)-1H-1,2,3-triazol-4-yl][5-(2,2,2-trifluoroethoxy)pyridin-2-yl]methyl}acetamide (32.00 mg, 0.0650 mmol) in 0.5 ml of anhydrous CH₃CN at RT was added diisopropylethylamine (0.0450 ml, 0.260 mmol), diisopropylethylamine dihydrogen fluoride complex (0.0180 ml, 0.0980 mmol), and perfluorobutanesulfonyl fluoride (0.0230 ml, 0.130 mmol).

The resulting solution was stirred at room temperature for 16 hours. The reaction mixture was diluted with water and extracted with CH$_2$Cl$_2$. The combined organic layers were washed with brine, dried over anhydrous Na$_2$SO$_4$ and filtered. The filtrate was concentrated in vacuum. Purification by preparative HPLC (20-90% CH$_3$CN/H$_2$O over 30 min, 0.05% added TFA, C18 column) to afford 0.0171 g (53%) of the title compound. $^1$H NMR (CDCl$_3$, 400 MHz) δ 8.245 (d, J=2.93 Hz, 1H), 7.569 (s, 1H), 7.527 (d, J=7.14 Hz, 1H), 7.369 (m, 2H), 7.270 (m, 1H), 7.225 (m, 2H), 6.336 (d, J=7.14 Hz, 1H), 4.800 (AB q, J=4.53 Hz, 1H), 4.682 (AB q, J=4.21 Hz, 1H), 4.617 (AB q, J=4.53 Hz, 1H), 4.550 (AB q, J=4.67 Hz, 1H), 4.378 (q, J=7.88 Hz, 2H), 3.623 (s, 2H), 3.086 (br s, 1H), 1.314 (s, 9H). ES-MS [M+1]$^+$: 494.2.

INTERMEDIATE 43

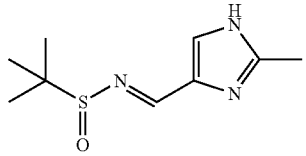

2-Methyl-N-((1E)-(2-methyl-1H-imidazol-4-yl)methylene]propane-2-sulfinamide

To a 50 ml round bottom flask equipped with a magnetic stir bar were added 2-methyl-1H-imidazole-4-carbaldehyde (0.710 g, 5.720 mmol), 4-tert-butylsulfinamide (0.693 g, 5.720 mmol), Cu$_2$SO$_4$ (1.825 g, 11.44 mmol), and titanium (IV) ethoxide (1.617 ml, 7.800 mmol) into 15.0 ml of CH$_2$Cl$_2$. The resulting solution was stirred at room temperature for 4 hours. The mixture was filtered through a celite pad. The filtrate was concentrated in vacuum. Purification by flash chromatography (SiO$_2$, 50-100% ethyl acetate in hexanes, gradient) gave the title compound as a white solid (1.170 g, 99%). $^1$H NMR (CDCl$_3$, 400 MHz) δ 8.388 (s, 1H), 7.450 (s, 1H), 3.438 (s, 1H), 2.449 (s, 3H), 1.232 (s, 9H). ES-MS [M+1]$^+$: 214.1.

INTERMEDIATE 44

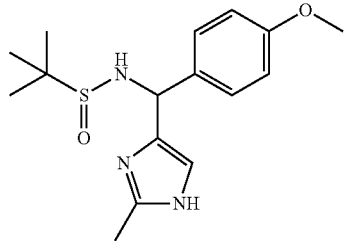 [SMILES: COc1ccc(C(NS(=O)C(C)(C)C)c2c[nH]c(C)n2)cc1]

N-[(4-methoxyphenyl)(2-methyl-1H-imidazol-4-yl)methyl]-2-methylpropane-2-sulfinamide To a 100 ml round bottom flask containing –78° C. solution of 2-methyl-N-((1E)-(2-methyl-1H-imidazol-4-yl)methylene]propane-2-sulfinamide (1.170 g, 5.490 mmol) in 25.0 ml of CH$_2$Cl$_2$ was added dropwise 1.0 N 4-methoxyphenylmagnesium bromide in THF (8.230 ml, 8.230 mmol). The resulting solution was stirred at –78° C. for 1 hour. The reaction mixture was quenched with saturated NH$_4$Cl and extracted with CH$_2$Cl$_2$. The combined organic layers were washed with brine, dried over anhydrous Na$_2$SO$_4$ and filtered. The filtrate was concentrated in vacuum. Purification by flash chromatography (SiO$_2$, 0-4% methanol in CH$_2$Cl$_2$, gradient) gave the title compound as a white solid (0.735 g, 42%). $^1$H NMR (CDCl$_3$, 400 MHz) δ 7.270 (m, 2H), 6.849 (m, 2H), 6.405 (s, 1H), 5.451 (d, J=6.04 Hz, 1H), 4.307 (d, J=6.05 Hz, 1H), 3.791 (s, 3H), 3.433 (s, 1H), 2.282 (s, 3H), 1.251 (s, 9H). ES-MS [M+1]$^+$: 322.3.

INTERMEDIATE 45

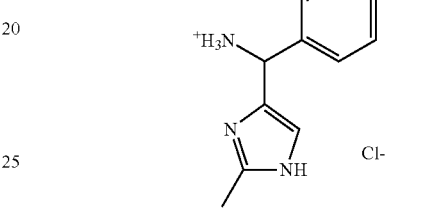

(4-Methoxyphenyl)(2-methyl-1H-imidazol-4-yl)methanaminium chloride

To a solution of N-[(4-methoxyphenyl)(2-methyl-1H-imidazol-4-yl)methyl]-2-methylpropane-2-sulfinamide (0.735 mg, 2.287 mmol) in 10.0 ml of MeOH was added 2.0N HCl in Et$_2$O (11.43 ml, 22.87 mmol), and the mixture was stirred at RT for 30 min. Solvent removed and the residue was dried under vacuum to give the crude title compound (0.568 g, 98%). ES-MS [M+1]$^+$: m/z 218.1. This intermediate was carried over to the next step without further purification and characterization.

EXAMPLE 19

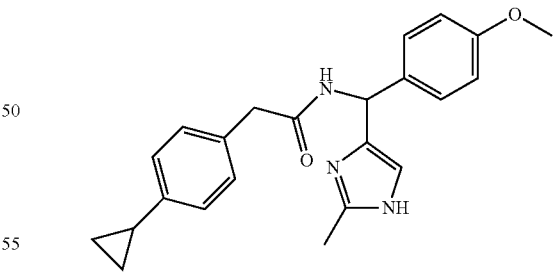

2-(4-Cyclopropylphenyl)-N-[(4-methoxyphenyl)(2-methyl-1H-imidazol-4-yl)methyl]acetamide To a 50 ml round bottom flask equipped with a magnetic stir bar were added (4-methoxyphenyl)(2-methyl-1H-imidazol-4-yl)methanaminium chloride (0.350 g, 1.206 mmol), 4-cyclopropylphenylacetic acid (0.213 mg, 1.206 mmol), 1-(3-dimethylaminopropyl)-3-ethylcarbodiimide hydrochloride (0.231 g, 1.206 mmol), 1-hydroxy-7-azabenzotriazole (0.164 mg, 1.206 mmol) and triethylamine (0.336 ml, 2.412 mmol) into 10.0 ml of $CH_2Cl_2$. The resulting solution was stirred at room temperature for 16 hours. The reaction mixture was diluted with water and the two layers were separated. The aqueous layer was extracted with $CH_2Cl_2$. The combined organic layers were washed with brine, dried over anhydrous $Na_2SO_4$ and filtered. The filtrate was concentrated in vacuum. Purification by flash chromatography ($SiO_2$, 0-10% methanol in $CH_2Cl_2$, gradient) gave the title compound as a white solid (0.260 g, 57%). $^1$H NMR ($CDCl_3$, 400 MHz) δ 7.151 (m, 4H), 7.021 (d, J=8.24 Hz, 2H), 7.820 (d, J=8.60 Hz, 2H), 6.459 (s, 1H), 6.459 (br s, 1H), 5.989 (d, J=7.32 Hz, 1H), 3.778 (s, 3H), 3.552 (s, 2H), 2.355 (s, 3H), 1.870 (m, 1H), 0.950 (m, 2H), 0.669 (m, 2H). ES-MS [M+1]$^+$: 376.3.

EXAMPLE 20

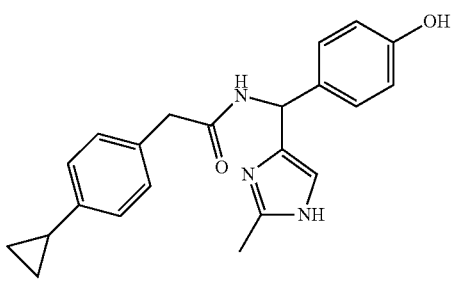 [SMILES: Cc1nc(C(NC(=O)Cc2ccc(C3CC3)cc2)c2ccc(O)cc2)c[nH]1]

2-(4-Cyclopropylphenyl)-N-[(4-hydroxyphenyl)(2-methyl-1H-imidazol-4-yl)methyl]acetamide To a 10 ml round bottom flask containing −78° C. solution of 2-(4-cyclopropylphenyl)-N-[(4-methoxyphenyl)(2-methyl-1H-imidazol-4-yl)methyl]acetamide (80.00 mg, 0.213 mmol) in 2.0 ml of $CH_2Cl_2$ was added drop-wise 1.0 N $BBr_3$ in $CH_2Cl_2$ (1.065 ml, 1.065 mmol). The resulting solution was stirred at −10° C. for 2 hours. The reaction mixture was quenched with diethyl ether. Water was added and extracted with $CH_2Cl_2$. The combined organic layers were washed with brine, dried over anhydrous $Na_2SO_4$ and filtered. The filtrate was concentrated in vacuum. Purification by preparative HPLC (10-90% $CH_3CN/H_2O$ over 30 min, 0.05% added TFA, C18 column) to afford 15.20 mg (20%) of the title compound. $^1$H NMR ($CD_3OD$, 400 MHz) δ 7.136 (m, 4H), 7.012 (m, 2H), 6.938 (d, J=1.10 Hz, 1H), 6.797 (m, 2H), 6.067 (s, 1H), 3.523 (s, 2H), 3.344 (s, 1H), 2.552 (s, 3H), 1.868 (m, 1H), 0.932 (m, 2H), 0.635 (m, 2H). ES-MS [M+1]$^+$: 362.3.

EXAMPLE 21

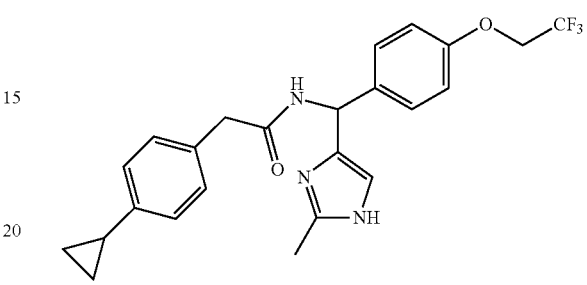

2-(4-Cyclopropylphenyl)-N-[(4-hydroxyphenyl)(2-methyl-1H-imidazol-4-yl)[4-(2,2,2-trifluoroethoxy)phenyl]methyl}acetamide To a 5 ml round bottom flask containing solution of 2-(4-cyclopropylphenyl)-N-[(4-hydroxyphenyl)(2-methyl-1H-imidazol-4-yl)methyl]acetamide (10.00 mg, 0.0280 mmol) in 0.3 ml of $CH_2Cl$ at RT was added $Cs_2CO_3$ (18.03 mg, 0.0550 mmol). To the mixture was added dropwise 2,2,2-trifluoroethyl trifluoromethanesulfonate (6.420 mg, 0.0280 mmol). The resulting solution was stirred at RT for 16 hours. Filtered and the filtrate was purified by preparative HPLC (10-90% $CH_3CN/H_2O$ over 30 min, 0.05% added TFA, C18 column) to afford 5.60 mg (46%) of the title compound. $^1$H NMR ($CDCl_3$, 400 MHz) δ 8.448 (d, J=7.32 Hz, 1H), 7.152 (d, J=8.60 Hz, 2H), 7.071 (d, J=8.06 Hz, 2H), 6.936 (d, J=8.05 Hz, 2H), 6.874 (d, J=8.61 Hz, 2H), 6.592 (s, 1H), 6.109 (d, J=7.88 Hz, 1H), 4.308 (q, J=8.06 Hz, 2H), 3.544 (s, 2H), 2.395 (s, 3H), 1.798 (m, 1H), 0.918 (m, 2H), 0.590 (m, 2H). ES-MS [M+1]$^+$: 444.2.

TABLE 1

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 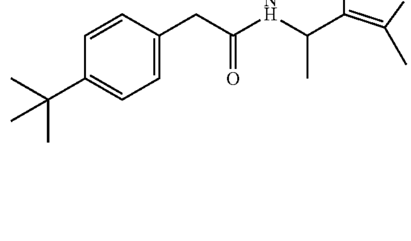 | 2-(4-tert-butylpheny])-N-[1-(2,5-dimethyl-1,3-thiazol-4-yl)ethyl]acetamide | 331.1 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 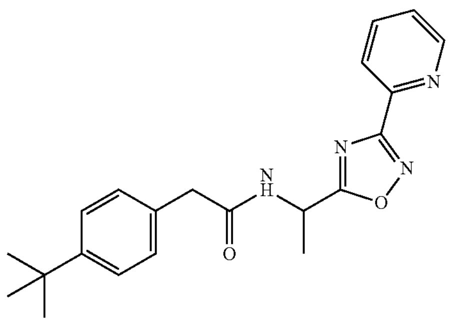 [SMILES: CC(NC(=O)Cc1ccc(C(C)(C)C)cc1)c1nc(-c2ccccn2)no1] | 2-(4-tert-butylphenyl)-N-{1-[3-(pyridin-2-yl)-1,2,4-oxadiazol-5-yl]ethyl}acetamide | 365.1 |
| 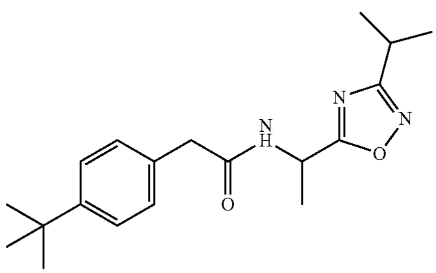 [SMILES: CC(C)c1noc(C(C)NC(=O)Cc2ccc(C(C)(C)C)cc2)n1] | 2-(4-tert-butylphenyl)-N-{1-[3-(propan-2-yl)-1,2,4-oxadiazol-5-yl]ethyl}acetamide | 330.2 |
| 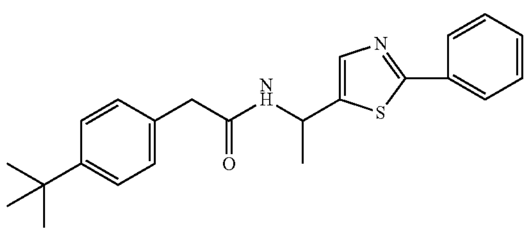 [SMILES: CC(NC(=O)Cc1ccc(C(C)(C)C)cc1)c1cnc(-c2ccccc2)s1] | 2-(4-tert-butylphenyl)-N-[1-(2-phenyl-1,3-thiazol-5-yl)ethyl]acetamide | 379.1 |
| 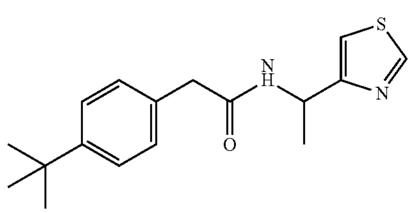 [SMILES: CC(NC(=O)Cc1ccc(C(C)(C)C)cc1)c1cscn1] | 2-(4-tert-butylphenyl)-N-[1-(1,3-thiazol-4-yl)ethyl]acetamide | 303.1 |
| 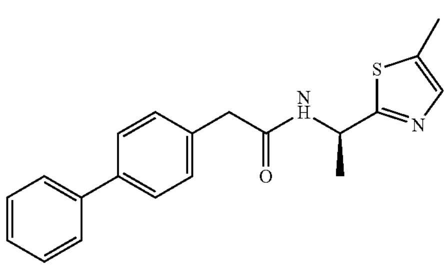 [SMILES: Cc1cnc([C@@H](C)NC(=O)Cc2ccc(-c3ccccc3)cc2)s1] | 2-(biphenyl-4-yl)-N-[(1R)-1-(5-methyl-1,3-thiazol-2-yl)ethyl]acetamide | 337.1 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 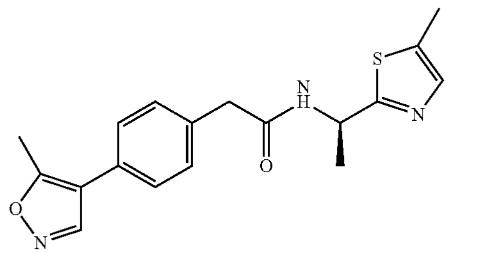 [SMILES: Cc1cnc([C@@H](C)NC(=O)Cc2ccc(-c3cnoc3C)cc2)s1] | 2-[4-(5-methylisoxazol-4-yl)phenyl]-N-[(1R)-1-(5-methyl-1,3-thiazol-2-yl)ethyl]acetamide | 342.1 |
| 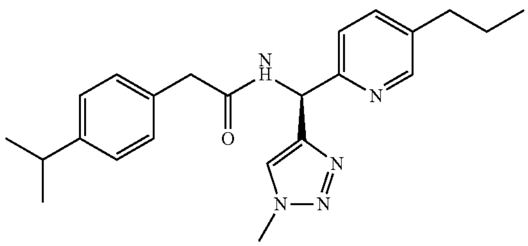 [SMILES: CCCc1ccc([C@H](NC(=O)Cc2ccc(C(C)C)cc2)c2cn(C)nn2)nc1] | N-[(S)-(1-methyl-1H-1,2,3-triazol-4-yl)(5-propylpyridin-2-yl)methyl]-2-[4-(propan-2-yl)phenyl]acetamide | 392.3 |
|  | N-[(S)-(5-amino-1,3,4-oxadiazol-2-yl)(phenyl)methyl]-2-[4-(propan-2-yl)phenyl]acetamide | 351.1 |
| 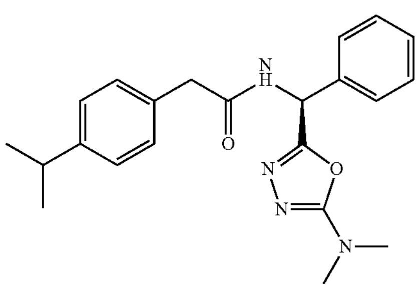 [SMILES: CC(C)c1ccc(CC(=O)N[C@@H](c2ccccc2)c2nnc(N(C)C)o2)cc1] | N-[(S)-[5-(dimethylamino)-1,3,4-oxadiazol-2-yl](phenyl)methyl]-2-[4-(propan-2-yl)phenyl]acetamide | 379.2 |
| 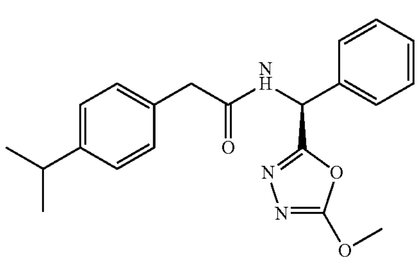 [SMILES: COc1nnc([C@@H](NC(=O)Cc2ccc(C(C)C)cc2)c2ccccc2)o1] | N-[(S)-5-methoxy-1,3,4-oxadiazol-2-yl)(phenyl)methyl]-2-[4-(propan-2-yl)phenyl]acetamide | 366.1 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 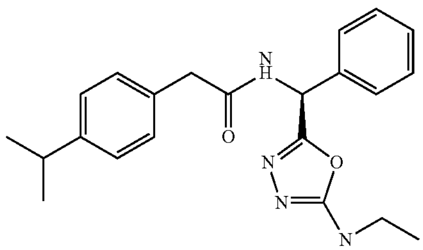 [SMILES: CCNc1nnc([C@@H](NC(=O)Cc2ccc(C(C)C)cc2)c2ccccc2)o1] | N-[(S)-[5-(ethylamino)-1,3,4-oxadiazol-2-yl](phenyl)methyl]-2-[4-(propan-2-yl)phenyl]acetamide | 379.2 |
| 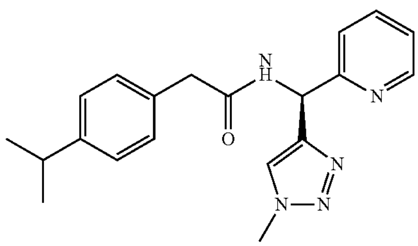 [SMILES: CC(C)c1ccc(CC(=O)N[C@@H](c2ccccn2)c2cn(C)nn2)cc1] | N-[(S)-(1-methyl-1H-1,2,3-triazol-4-yl)(pyridin-2-yl)methyl]-2-[4-(propan-2-yl)phenyl]acetamide | 350.2 |
| 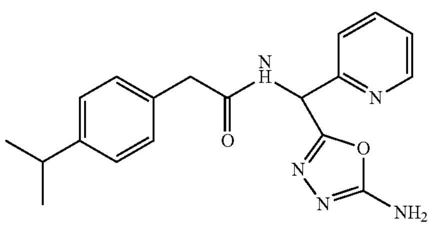 [SMILES: CC(C)c1ccc(CC(=O)NC(c2ccccn2)c2nnc(N)o2)cc1] | N-[(5-amino-1,3,4-oxadiazol-2-yl)(pyridin-2-yl)methyl]-2-[4-(propan-2-yl)phenyl]acetamide | 352.1 |
| | N-[phenyl(2H-tetrazol-5-yl)methyl]-2-[4-(propan-2-yl)phenyl]acetamide | 336.1 |
| 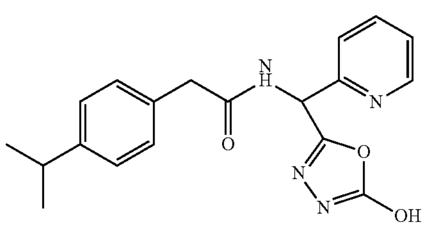 [SMILES: CC(C)c1ccc(CC(=O)NC(c2ccccn2)c2nnc(O)o2)cc1] | N-[(5-hydroxy-1,3,4-oxadiazol-2-yl)(pyridin-2-yl)methyl]-2-[4-(propan-2-yl)phenyl]acetamide | 353.1 |
| 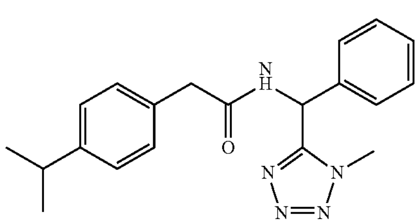 [SMILES: CC(C)c1ccc(CC(=O)NC(c2ccccc2)c2nnnn2C)cc1] | N-[(1-methyl-1H-tetrazol-5-yl)(phenyl)methyl]-2-[4-(propan-2-yl)phenyl]acetamide | 350.1 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 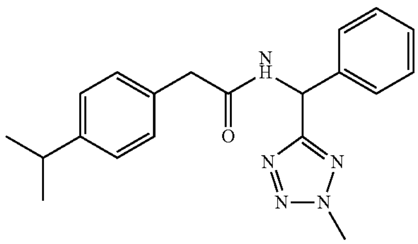 [SMILES: CC(C)c1ccc(CC(=O)NC(c2ccccc2)c2nnn(C)n2)cc1] | N-[(2-methyl-2H-tetrazol-5-yl)(phenyl)methyl]-2-[4-(propan-2-yl)phenyl]acetamide | 350.1 |
| 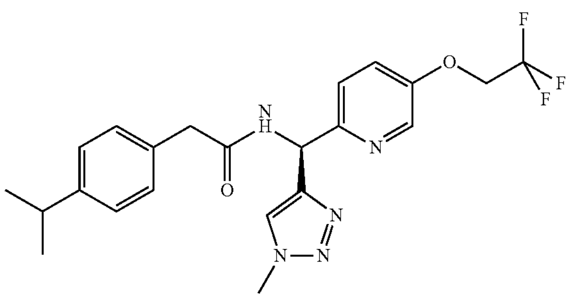 [SMILES: CC(C)c1ccc(CC(=O)N[C@@H](c2ccc(OCC(F)(F)F)cn2)c2cn(C)nn2)cc1] | N-{(S)-(1-methyl-1H-1,2,3-triazol-4-yl)[5-(2,2,2-trifluoroethoxy)pyridin-2-yl]methyl}-2-[4-(propan-2-yl)phenyl]acetamide | 448.1 |
| 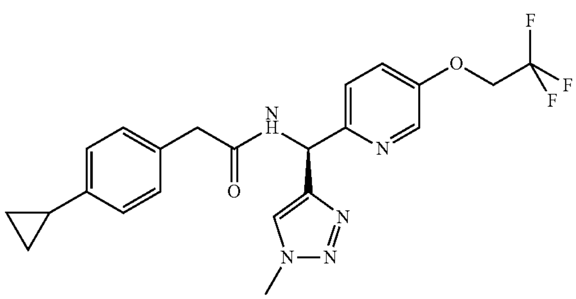 [SMILES: Cn1cc([C@@H](NC(=O)Cc2ccc(C3CC3)cc2)c2ccc(OCC(F)(F)F)cn2)nn1] | 2-(4-cyclopropylphenyl)-N-{(S)-(1-methyl-1H-1,2,3-triazol-4-yl)[5-(2,2,2-trifluoroethoxy)pyridin-2-yl]methyl}acetamide | 446.1 |
| 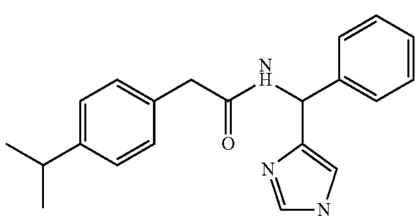 [SMILES: CC(C)c1ccc(CC(=O)NC(c2ccccc2)c2c[nH]cn2)cc1] | N-[1H-imidazol-4-yl(phenyl)methyl]-2-[4-(propan-2-yl)phenyl]acetamide | 334.1 |
| 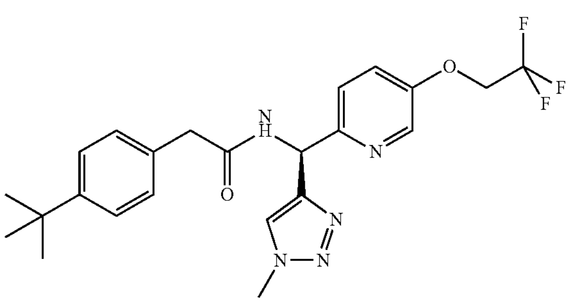 [SMILES: Cn1cc([C@@H](NC(=O)Cc2ccc(C(C)(C)C)cc2)c2ccc(OCC(F)(F)F)cn2)nn1] | 2-(4-tert-butylphenyl)-N-{(S)-(1-methyl-1H-1,2,3-triazol-4-yl)[5-(2,2,2-trifluoroethoxy)pyridin-2-yl]methyl}acetamide | 462.3 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 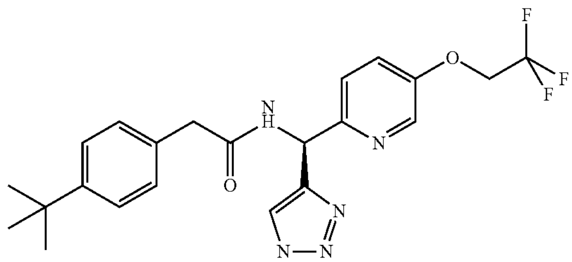 [SMILES: CC(C)(C)c1ccc(CC(=O)N[C@@H](c2ccc(OCC(F)(F)F)cn2)c2c[nH]nn2)cc1] | 2-(4-tert-butylphenyl)-N-{(S)-1H-1,2,3-triazol-4-yl[5-(2,2,2-trifluoroethoxy)pyridin-2-yl]methyl}acetamide | 448.1 |
| 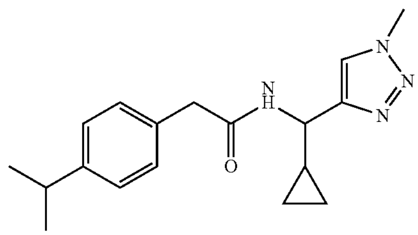 [SMILES: CC(C)c1ccc(CC(=O)NC(c2cn(C)nn2)C2CC2)cc1] | N-[cyclopropyl(1-methyl-1H-1,2,3-triazol-4-yl)methyl]-2-[4-(propan-2-yl)phenyl]acetamide | 313.1 |
| 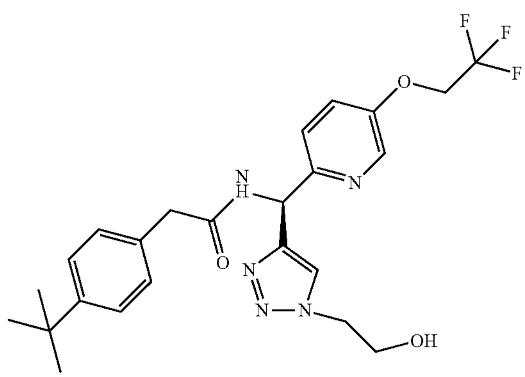 [SMILES: CC(C)(C)c1ccc(CC(=O)N[C@@H](c2ccc(OCC(F)(F)F)cn2)c2cn(CCO)nn2)cc1] | 2-(4-tert-butylphenyl)-N-{(S)-[1-(2-hydroxyethyl)-1H-1,2,3-triazol-4-yl][5-(2,2,2-trifluoroethoxy)pyridin-2-yl]methyl}acetamide | 492.3 |
| 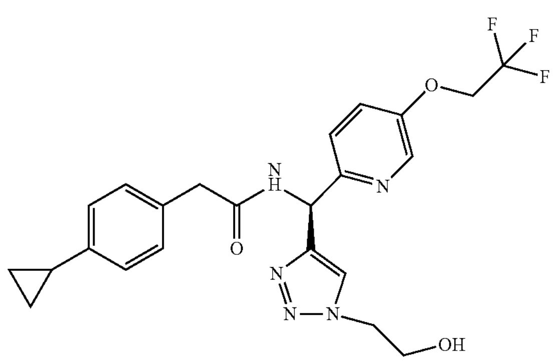 [SMILES: O=C(Cc1ccc(C2CC2)cc1)N[C@@H](c1ccc(OCC(F)(F)F)cn1)c1cn(CCO)nn1] | 2-(4-cyclopropylphenyl)-N-{(S)-[1-(2-hydroxyethyl)-1H-1,2,3-triazol-4-yl][5-(2,2,2-trifluoroethoxy)pyridin-2-yl]methyl}acetamide | 476.2 |
| | 2-(4-cyclopropylphenyl)-N-[1H-imidazol-4-yl(4-methoxyphenyl)methyl]acetamide | 362.1 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 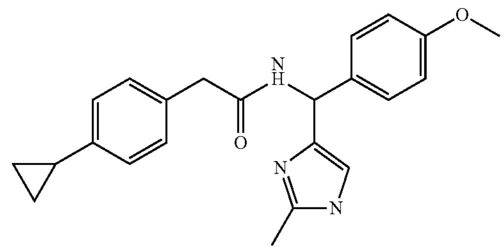 [SMILES: COc1ccc(C(NC(=O)Cc2ccc(C3CC3)cc2)c2c[nH]c(C)n2)cc1] | 2-(4-cyclopropylphenyl)-N-[(4-methoxyphenyl)(2-methyl-1H-imidazol-4-yl)methyl]acetamide | 376.3 |
| 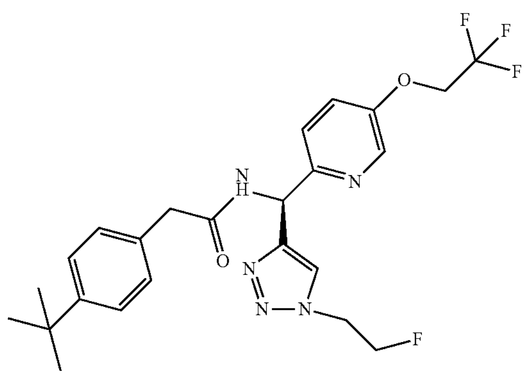 [SMILES: CC(C)(C)c1ccc(CC(=O)N[C@@H](c2ccc(OCC(F)(F)F)cn2)c2cn(CCF)nn2)cc1] | 2-(4-tert-butylphenyl)-N-{(S)-[1-(2-fluoroethyl)-1H-1,2,3-triazol-4-yl][5-(2,2,2-trifluoroethoxy)pyridin-2-yl]methyl}acetamide | 494.2 |
| 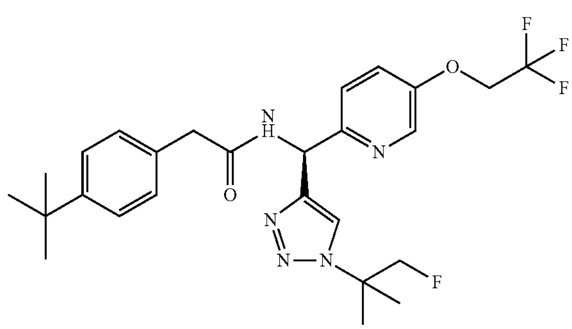 [SMILES: CC(C)(C)c1ccc(CC(=O)N[C@@H](c2ccc(OCC(F)(F)F)cn2)c2cn(C(C)(C)CF)nn2)cc1] | 2-(4-tert-butylphenyl)-N-{(S)-[1-(1-fluoro-2-methylpropan-2-yl)-1H-1,2,3-triazol-4-yl][5-(2,2,2-trifluoroethoxy)pyridin-2-yl]methyl}acetamide | 522.2 |
| 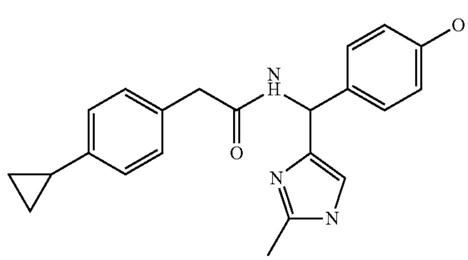 [SMILES: Cc1nc(C(NC(=O)Cc2ccc(C3CC3)cc2)c2ccc(O)cc2)c[nH]1] | 2-(4-cyclopropylphenyl)-N-[(4-hydroxyphenyl)(2-methyl-1H-imidazol-4-yl)methyl]acetamide | 362.3 |

TABLE 1-continued

The following compounds were prepared using the foregoing methodology, but substituting the appropriately substituted reagent, such as organometallic or amine, as described in the foregoing examples. The requisite starting materials were commercialy available, described in the literature or readily synthesized by one skilled in the art of organic synthesis without undue experimentation.

| Structure | Name | M + 1 |
|---|---|---|
| 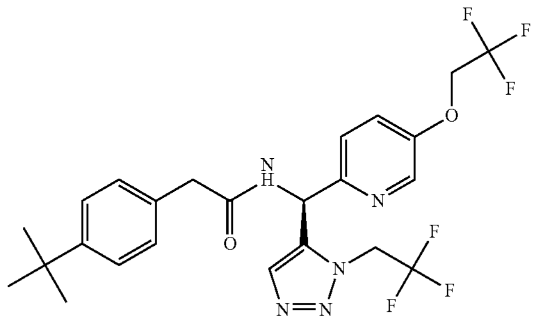 [SMILES: CC(C)(C)c1ccc(CC(=O)N[C@@H](c2ccc(OCC(F)(F)F)cn2)c2cnnn2CC(F)(F)F)cc1] | 2-(4-tert-butylphenyl)-N-{(S)-[5-(2,2,2-trifluoroethoxy)pyridin-2-yl][1-(2,2,2-trifluoroethyl)-1H-1,2,3-triazol-5-yl]methyl}acetamide | 530.2 |
| 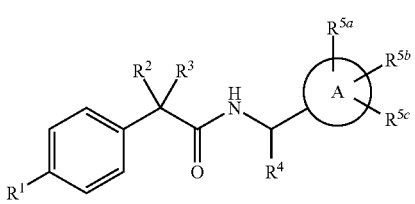 | 2-(4-cyclopropylphenyl)-N-[(S)-(1-methyl-1H-1,2,3-triazol-4-yl)(4-propylphenyl)methyl]acetamide | 389.1 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula I:

I wherein:
A is pyridyl;
$R^1$ is selected from the group consisting of:
  (1) $C_{1-6}$alkyl, which is unsubstituted or substituted with halo, $C_{3-6}$cycloalkyl or phenyl,
  (2) $C_{3-6}$cycloalkyl, which is unsubstituted or substituted with halo, $C_{3-6}$cycloalkyl or phenyl, and
  (3) phenyl, which is unsubstituted or substituted with one or more substituents selected from $R^6$;
$R^2$ and $R^3$ are independently selected from the group consisting of:
  (1) hydrogen,
  (2) halogen,
  (3) $C_{1-6}$alkyl, which is unsubstituted or substituted with halo, $C_{3-6}$cycloalkyl or phenyl, and
  (4) $C_{3-6}$cycloalkyl, which is unsubstituted or substituted with halo, $C_{3-6}$cycloalkyl or phenyl;
$R^4$ is 1,2,3-triazolyl, which is unsubstituted or substituted with one or more substituents selected from $R^6$;
$R^{5a}$, $R^{5b}$ and $R^{5c}$ are independently selected from the group consisting of:
  (1) hydrogen,
  (2) halogen,
  (3) hydroxyl,
  (4) $C_{1-6}$alkyl, which is unsubstituted or substituted with halogen, hydroxyl, phenyl, —O—$C_{1-6}$ alkyl, —O—(CO)$C_{1-6}$alkyl, or $C_{3-6}$ cycloalkyl,
  (5) —O—$C_{1-6}$alkyl, which is unsubstituted or substituted with halogen, hydroxyl, phenyl, —O—$C_{1-6}$ alkyl, —O—(CO)$C_{1-6}$alkyl, or $C_{3-6}$cycloalkyl, and
  (6) —$C_{2-4}$alkenyl;
$R^6$ is selected from the group consisting of:
  (1) hydroxyl,
  (2) halogen,
  (3) $C_{1-6}$alkyl, which is unsubstituted or substituted with halogen, hydroxyl, phenyl, —O—$C_{1-6}$alkyl, —O—(CO)$C_{1-6}$alkyl, —(CO)—O—$C_{1-6}$alkyl, or $C_{3-6}$cycloalkyl,
  (4) —$C_{3-6}$cycloalkyl, which is unsubstituted or substituted with halogen, hydroxyl, phenyl, —O—$C_{1-6}$ alkyl, —O—(CO)$C_{1-6}$alkyl, or $C_{3-6}$cycloalkyl,
  (5) —O—$C_{1-6}$alkyl,
  (6) —O(C=O)—$C_{1-6}$alkyl,
  (7) —NH—$C_{1-6}$ alkyl,
  (8) —$NH_2$,
  (9) phenyl, which is unsubstituted or substituted with halogen, hydroxyl, phenyl, —O—$C_{1-6}$ alkyl, —O—(CO)$C_{1-6}$alkyl, or $C_{3-6}$ cycloalkyl,
  (11) —$CO_2H$, and
  (12) —CN;
or a pharmaceutically acceptable salt thereof.

2. The compound of claim 1 wherein $R^1$ is selected from the group consisting of:
  (1) $C_{1-6}$alkyl, and
  (2) $C_{3-6}$cycloalkyl.

3. The compound of claim 2 wherein $R^1$ is selected from the group consisting of:
  (1) isopropyl,
  (2) tert-butyl, and
  (2) cyclopropyl.

4. The compound of claim 1 wherein $R^2$ is hydrogen and $R^3$ is hydrogen.

5. The compound of claim 1 wherein $R^4$ is triazolyl, which is unsubstituted or substituted with one or more substitutents selected from the group consisting of:
  (1) halogen,
  (2) hydroxyl, and
  (3) $C_{1-6}$alkyl, which is unsubstituted or substituted with halogen, hydroxyl, phenyl, —O—$C_{1-6}$alkyl, —O—(CO)$C_{1-6}$alkyl, or $C_{3-6}$cycloalkyl.

6. The compound of claim 1 wherein $R^{5a}$, $R^{5b}$ and $R^{5c}$ are independently selected from the group consisting of:
  (1) hydrogen,
  (2) halogen,
  (3) hydroxyl,
  (4) $C_{1-6}$alkyl, which is unsubstituted or substituted with halogen, hydroxyl, phenyl, —O—$C_{1-6}$alkyl, —O—(CO)$C_{1-6}$alkyl, or $C_{3-6}$cycloalkyl, and
  (5) —$C_{2-4}$alkenyl.

7. The compound of claim 6 wherein $R^{5b}$ is hydrogen, $R^{5c}$ is hydrogen and $R^{5a}$ is independently selected from the group consisting of:
  (1) hydrogen,
  (2) fluoro,
  (3) chloro,
  (4) bromo,
  (5) hydroxyl,
  (6) —$CH_3$,
  (7) —$CH_2OH$,
  (8) —$CH_2CH_3$,
  (9) —$CH_2$=$CH_2$, and
  (10) —$CH_2CH_2CH_3$.

8. A compound which is selected from the group consisting of:
  N-[(S)-(5-bromopyridin-2-yl)(1-methyl-1H-1,2,3-triazol-4-yl)methyl]-2-(4-isopropylphenyl)acetamide;
  2-(4-isopropylphenyl)-N-[(S)-(1-methyl-1H-1,2,3-triazol-4-yl)(5-propylpyridin-2-yl)methyl]acetamide;
  N-{(S)-(1-methyl-1H-1,2,3-triazol-4-yl)[4-(2,2,2-trifluoroethoxy)phenyl]methyl}-2-[4-(propan-2-yl)phenyl]acetamide;
  2-(4-tert-butylphenyl)-N-{(S)-[1-(4-methoxybenzyl)-1H-1,2,3-triazol-4-yl][5-(2,2,2-trifluoroethoxy)pyridin-2-yl]methyl}acetamide;
  2-(4-tert-butylphenyl)-N-{(S)-1H-1,2,3-triazol-4-yl[5-(2,2,2-trifluoroethoxy)pyridin-2-yl]methyl}acetamide;
  Methyl 2-(4-{(S)-{[(4-tert-butylphenyl)acetyl]amino}[5-(2,2,2-trifluoroethoxy)pyridin-2-yl]methyl}-1H-1,2,3-triazol-1-yl)-2-methylpropanoate;
  2-(4-tert-butylphenyl)-N-{(S)-[1-(2-hydroxy-1,1-dimethylethyl)-1H-1,2,3-triazol-4-yl][5-(2,2,2-trifluoroethoxy)pyridin-2-yl]methyl}acetamide;
  2-(4-tert-butylphenyl)-N-{(S)-[1-(2-fluoro-1,1-dimethylethyl)-1H-1,2,3-triazol-4-yl][5-(2,2,2-trifluoroethoxy)pyridin-2-yl]methyl}acetamide;
  2-(4-tert-Butylphenyl)-N-{(S)-[1-(2-hydroxyethyl)-1H-1,2,3-triazol-4-yl][5-(2,2,2-trifluoroethoxy)pyridin-2-yl]methyl}acetamide;
  2-(4-tert-Butylphenyl)-N-{(S)-[1-(2-fluoroethyl)-1H-1,2,3-triazol-4-yl][5-(2,2,2-trifluoroethoxy)pyridin-2-yl]methyl}acetamide;
  N-[(S)-(1-methyl-1H-1,2,3-triazol-4-yl)(5-propylpyridin-2-yl)methyl]-2-[4-(propan-2-yl)phenyl]acetamide;
  N-{(S)-(1-methyl-1H-1,2,3-triazol-4-yl)[5-(2,2,2-trifluoroethoxy)pyridin-2-yl]methyl}-2-[4-(propan-2-yl)phenyl]acetamide;
  2-(4-cyclopropylphenyl)-N-{(S)-(1-methyl-1H-1,2,3-triazol-4-yl)[5-(2,2,2-trifluoroethoxy)pyridin-2-yl]methyl}acetamide;
  2-(4-tert-butylphenyl)-N-{(S)-(1-methyl-1H-1,2,3-triazol-4-yl)[5-(2,2,2-trifluoroethoxy)pyridin-2-yl]methyl}acetamide;
  2-(4-tert-butylphenyl)-N-{(S)-1H-1,2,3-triazol-4-yl[5-(2,2,2-trifluoroethoxy)pyridin-2-yl]methyl}acetamide;
  2-(4-tert-butylphenyl)-N-{(S)-[1-(2-hydroxyethyl)-1H-1,2,3-triazol-4-yl][5-(2,2,2-trifluoroethoxy)pyridin-2-yl]methyl}acetamide;
  2-(4-cyclopropylphenyl)-N-{(S)-[1-(2-hydroxyethyl)-1H-1,2,3-triazol-4-yl][5-(2,2,2-trifluoroethoxy)pyridin-2-yl]methyl}acetamide;
  2-(4-tert-butylphenyl)-N-{(S)-[1-(2-fluoroethyl)-1H-1,2,3-triazol-4-yl][5-(2,2,2-trifluoroethoxy)pyridin-2-yl]methyl}acetamide;
  2-(4-tert-butylphenyl)-N-{(S)-[1-(1-fluoro-2-methylpropan-2-yl)-1H-1,2,3-triazol-4-yl][5-(2,2,2-trifluoroethoxy)pyridin-2-yl]methyl}acetamide; and
  2-(4-tert-butylphenyl)-N-{(S)-[5-(2,2,2-trifluoroethoxy)pyridin-2-yl][1-(2,2,2-trifluoroethyl)-1H-1,2,3-triazol-5-yl]methyl}acetamide;
or a pharmaceutically acceptable salt thereof.

9. A pharmaceutical composition which comprises an inert carrier and a compound of claim 1 or a pharmaceutically acceptable salt thereof.

* * * * *